(12) United States Patent
Brewer et al.

(10) Patent No.: US 6,962,910 B2
(45) Date of Patent: Nov. 8, 2005

(54) SUPRAMOLECULAR COMPLEXES AS PHOTOACTIVATED DNA CLEAVAGE AGENTS

(75) Inventors: Karen Brewer, Blacksburg, VA (US); Shawn Swavey, Kettering, OH (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 309 days.

(21) Appl. No.: 10/355,258

(22) Filed: Jan. 31, 2003

(65) Prior Publication Data

US 2003/0180767 A1 Sep. 25, 2003

Related U.S. Application Data

(60) Provisional application No. 60/352,865, filed on Feb. 1, 2002.

(51) Int. Cl.[7] .............................................. A61K 31/555
(52) U.S. Cl. ...................................... 514/188; 514/184
(58) Field of Search .................................. 514/184, 188

(56) References Cited

U.S. PATENT DOCUMENTS 5,457,195 A * 10/1995 Sessler et al. .............. 540/472
6,630,128 B1 * 10/2003 Love et al. .............. 424/9.362

OTHER PUBLICATIONS

Goldman et al. (Editors). Cecil's Textbook of Medicine (Twenty–First Edition).W.B. Saunders Company. 2000. p. 1060–1074.*

* cited by examiner

Primary Examiner—Raymond J. Henley, III
Assistant Examiner—Leslie Alexandra Royds
(74) Attorney, Agent, or Firm—Whitham, Curtis & Christofferson, PC

(57) ABSTRACT

The invention provides supramolecular metal complexes as DNA cleaving agents. In the complexes, charge is transferred from one light absorbing metal (e.g. Ru or Os) to an electron accepting metal (e.g. Rh) via a bridging π-acceptor ligand. A bioactive metal-to-metal charge transfer state capable of cleaving DNA is thus generated. The complexes function when irradiated with low energy visible light with or without molecular oxygen.

10 Claims, 13 Drawing Sheets dpp bpm tpy $$-2e^- \updownarrow +2e^-$$

synthesized oxidation state $$+2e^- -2CT$$

$[(tpy)Ru^{II}Cl(BL)Rh^{I}(BL)Ru^{II}Cl(tpy)]^{3+}$ $$-1e^- \updownarrow +1e^-$$

$[(tpy)Ru^{II}Cl(BL^-)Rh^{I}(BL)Ru^{II}Cl(tpy)]^{2+}$ $$-1e^- \updownarrow +1e^-$$

$[(tpy)Ru^{II}Cl(BL^-)Rh^{I}(BL^-)Ru^{II}Cl(tpy)]^{+}$

SUPRAMOLECULAR COMPLEXES AS PHOTOACTIVATED DNA CLEAVAGE AGENTS

This application claims the benefit of Provisional Application No. 60/352,865, filed Feb. 1, 2002.

This invention was made using funds from a grant from the National Science Foundation having grant number CHE-9632713. The government may have certain rights in this invention.

DESCRIPTION

BACKGROUND OF THE INVENTION

1. Field of the Invention

The invention generally relates to photodynamic therapy agents. In particular, the invention provides tunable supramolecular metallic complexes which can be activated to cleave DNA by low energy light and in the absence of $O_2$.

2. Background of the Invention

Photodynamic therapy (PDT) is currently gaining acceptance for the treatment of hyperproliferating tissues such as cancers and non-malignant lesions. Significant emphasis has been placed on developing photochemical reagents capable of cleaving DNA for such purposes. Photochemical approaches are of particular interest as they offer reaction control and can be highly targeted.

One popular approach in the design of photodynamic agents involves the sensitization of molecular oxygen. Typically, such agents absorb light energy and transfer that energy to molecular oxygen to generate a reactive singlet oxygen state, $^1O_2$. The $^1O_2$ state is highly reactive and, in an intracellular environment, $^1O_2$ randomly reacts with and damages biomolecules and subcellular components, leading to potentially lethal damage to the cell. However, the use of such agents has several drawbacks. For example, the wavelengths of light that must be used to activate this type of photodynamic agent are short wavelength/high energy and cause extensive damage to healthy tissue adjacent to the targeted, hyperproliferating cells. The targeted cell may lyse, releasing $^1O_2$ into the immediate environment where it continues to react randomly with and damage healthy tissue in the area. Further, such agents require the presence of oxygen, the level of which is relatively low in an intracellular environment. Finally, there is an overall lack of flexibility in the design of such agents.

It is thus of interest to develop photosensitizing agents for photodynamic therapy with alternative mechanisms of action. In particular, it would be of benefit to have available photosensitizing agents that absorb and are activated by low energy light. The use of photosensitizing agents that absorb low energy light is less likely to cause unwanted collateral damage to non-targeted cells in a photodynamic therapy setting. In addition, it would be of benefit to have available photosensitizing agents that function efficiently in the absence of molecular oxygen as such agents would be particularly suitable for intracelluar use. Further, it would be highly desirable to have available tunable photosensitizing agents, i.e. photosensitizing agents with a flexible architectural motif that can be readily adjusted or tailored for use in specific applications.

SUMMARY OF THE INVENTION

The present invention provides novel metal-based DNA cleaving agents. The agents are supramolecular metallic complexes containing at least one metal to ligand charge transfer (MLCT) light absorbing metal, at least one bridging π-acceptor ligand, and an electron acceptor metal. The complexes are capable of effecting the cleavage of DNA upon exposure to low energy visible light, and do so in the absence of oxygen.

The invention provides new compositions of matter of the forms:

1) [(2,2'-bipyridine)$_2$Os(2,3-bis(2-pyridyl)pyrazine)RhCl$_2$ (2,3-bis(2-pyridyl)pyrazine)Os(2,2'-bipyridine)$_2$](X)$_5$, where X is a counterion selected from the group consisting of PF$_6^-$, Cl$^-$, Br$^-$, CF$_3$SO$_3^-$ and BF$_4^-$.

2) [(2,2':6',2"-terpyridine)RuCl(2,3-bis(2-pyridyl)pyrazine) RhCl$_2$(2,3-bis(2-pyridyl)pyrazine)RuCl(2,2':6',2"-terpyridine)](X)$_3$, where X is a counterion selected from the group consisting of PF$_6^-$, Cl$^-$, Br$^-$, CF$_3$SO$_3^-$ and BF$_4^-$; and 3) [(2,2':6',2"-terpyridine)RuCl(2,2'-bipyridimidine)RhCl$_2$ (2,2'-bipyridimidine)RuCl(2,2':6',2"-terpyridine)](X)$_3$, where X is a counterion selected from the group consisting of PF$_6^-$, Cl$^-$, Br$^-$, CF$_3$SO$_3^-$ and BF$_4^-$. The invention also provides composition, comprising at least one of the above compounds dissolved or dispersed in a carrier.

The invention further provides a method for cleaving DNA. The method includes the steps of combining the DNA with a supramolecular complex. The complex contains at least one metal to ligand charge transfer (MLCT) light absorbing metal, at least one bridging π-acceptor ligand, and an electron acceptor metal. The step of combining is carried out under conditions that allow the supramolecular complex to bind to the DNA, and the supramolecular complex is present in sufficient quantity to cleave said DNA. The second step of the method is exposing the DNA to light or radiant energy in an amount sufficient to activate the supramolecular complex to cleave the DNA. The metal to ligand charge transfer (MLCT) light absorbing metal may be, for example, ruthenium(II), osmium(III), rhenium(I), iron(II) or platinum(II). The bridging π-acceptor ligand may be, for example, 2,3-bis(2-pyridyl)pyrazine; 2,2'-bipyridimidine; 2,3-bis(2-pyridyl)quinoxaline; or 2,3,5,6,-tetrakis(2-pyridyl)pyrazine. The electron acceptor metal may be, for example, rhodium(III), platinum(IV), cobalt (III), or iridium(III). The supramolecular complex may further include at least one terminal π-acceptor ligand, in which case the terminal π-acceptor ligand may be, for example, 2,2'-bipyridine; 2,2':6',2"-terpyridine; triphenylphosphine; and 2,2'-phenylpyridine or diethylphenylphosphine. In a preferred embodiment, the light used to activate the complex is visible light.

The supramolecular complex utilized in the method may be, for example, [(2,2'-bipyridine)$_2$ Ru(2-pyridyl)pyrazine) RhCl$_2$(2-pyridyl)pyrazine)Ru(2,2'-bipyridine)$_2$](PF$_6$)$_5$; [(2, 2'-bipyridine)$_2$Os(2,3-bis(2-pyridyl)pyrazine)RhCl$_2$(2,3-bis (2-pyridyl)pyrazine)Os(2,2'-bipyridine)$_2$](PF$_6$)$_5$; [(2,2':6', 2"-terpyridine)RuCl(2,3-bis(2-pyridyl)pyrazine)RhCl$_2$(2,3-bis(2-pyridyl)pyrazine)RuCl(2,2':6',2"-terpyridine)](PF$_6$)$_3$; or [(2,2':6',2"-terpyridine)RuCl(2,2'-bipyridimidine)RhCl$_2$ (2,2'-bipyridimidine)RuCl(2,2':6',2"-terpyridine)](PF$_6$)$_3$. In addition, the combining step of the method may occur within a hyperproliferating cell.

The invention also provides a composition for effecting the cleavage of DNA in hyperproliferating cells. The composition contains a supramolecular complex comprising at least one metal to ligand charge transfer (MLCT) light absorbing metal; at least one bridging π-acceptor ligand; and an electron acceptor metal. The metal to ligand charge transfer (MLCT) light absorbing metal may be ruthenium (II), osmium(III), rhenium(I), iron(II) or platinum(II). The bridging π-acceptor ligand may be 2,3-bis(2-pyridyl)pyrazine; 2,2'-bipyridimidine; 2,3-bis(2-pyridyl)quinoxaline; or 2,3,5,6,-tetrakis(2-pyridyl)pyrazine. The electron acceptor metal may be rhodium(III), platinum(IV), cobalt(III), or iridium(III). The supramolecular complex may further comprises at least one terminal π-acceptor ligand such as 2,2'-bipyridine; 2,2':6',2"-terpyridine; triphenylphosphine; and 2,2'-phenylpyridine or diethylphenylphosphine. The supromolecular complex may be dissolved or dispersed in a carrier.

The supramolecular complex in the composition may be [(2,2'-bipyridine)$_2$ Ru(2-pyridyl)pyrazine)RhCl$_2$(2-pyridyl)pyrazine)Ru(2,2'-bipyridine)$_2$](PF$_6$)$_5$; [(2,2'-bipyridine)$_2$Os(2,3-bis(2-pyridyl)pyrazine)RhCl$_2$(2,3-bis(2-pyridyl)pyrazine)Os(2,2'-bipyridine)$_2$](PF$_6$)$_5$; [(2,2':6',2"-terpyridine)RuCl(2,3-bis(2-pyridyl)pyrazine)RhCl$_2$(2,3-bis(2-pyridyl)pyrazine)RuCl(2,2':6',2"-terpyridine)](PF$_6$)$_3$; or [(2,2':6',2"-terpyridine)RuCl(2,2'-bipyridimidine)RhCl$_2$(2,2'-bipyridimidine)RuCl(2,2':6',2"-terpyridine)](PF$_6$)$_3$.

The invention further provides a method for decreasing the replication of hyperproliferating cells. The method includes the steps of delivering a supramolecular complex to the cells, the complex containing at least one metal to ligand charge transfer (MLCT) light absorbing metal; at least one bridging π-acceptor ligand; and an electron acceptor metal. The method further includes the step of applying light or radiant energy to the hyperproliferating cells. The step of applying light to the hyperproliferating cells induces the production of a metal-to-metal charge transfer state within the supramolecular complex. The metal-to-metal charge transfer state mediates the cleavage of DNA of the hyperproliferating cells, thereby causing a decrease in the replication of the hyperproliferating cells.

In the method, the at least one metal to ligand charge transfer (MLCT) light absorbing metal may be ruthenium (II), osmium(III), rhenium(I), iron(II) or platinum(II). The at least one bridging π-acceptor ligand may be 2,3-bis(2-pyridyl)pyrazine; 2,2'-bipyridimidine; 2,3-bis(2-pyridyl)quinoxaline; or 2,3,5,6,-tetrakis(2-pyridyl)pyrazine. The electron acceptor metal may be rhodium(III), platinum(IV), cobalt(III), or iridium(III). The supramolecular complex may further comprises at least one terminal π-acceptor ligand such as 2,2'-bipyridine; 2,2':6',2"-terpyridine; triphenylphosphine; and 2,2'-phenylpyridine and diethylphenylphosphine. The light may be visible light. The supramolecular complex may be [(2,2'-bipyridine)$_2$ Ru(2-pyridyl)pyrazine)RhCl$_2$(2-pyridyl)pyrazine)Ru(2,2'-bipyridine)$_2$](PF$_6$)$_5$; [(2,2'-bipyridine)$_2$Os(2,3-bis(2-pyridyl)pyrazine)RhCl$_2$(2,3-bis(2-pyridyl)pyrazine)Os(2,2'-bipyridine)$_2$](PF$_6$)$_5$; [(2,2':6',2"-terpyridine)RuCl(2,3-bis(2-pyridyl)pyrazine)RhCl$_2$(2,3-bis(2-pyridyl)pyrazine)RuCl(2,2':6',2"-terpyridine)](PF$_6$)$_3$; or [(2,2':6',2"-terpyridine)RuCl(2,2'-bipyridimidine)RhCl$_2$(2,2'-bipyridimidine)RuCl(2,2':6',2"-terpyridine)](PF$_6$)$_3$. The hyperproliferating cells may be cancer cells.

The invention further provides a method for decreasing the replication of hyperproliferating cells. The method comprises the steps of delivering to said hyperproliferating cells a supramolecular complex which contains at least one metal to ligand charge transfer (MLCT) light absorbing metal; at least one bridging π-acceptor ligand; and an electron acceptor metal, followed by the step of inducing the production of a metal-to-metal charge transfer state within the supramolecular complex by the application of light, thereby causing a decrease in replication of the hyperproliferating cells.

Figure 1A:
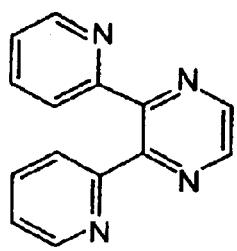
FIGS. 1A–C. Molecular structure of A, dpp; B, bpm; and C, tpy.

A, DNA Photocleavage of pUC18 using [{(bpy)$_2$Os(dpp)}$_2$RhCl$_2$](PF$_6$)$_5$:Lane 1 is the λ molecular weight standard, Lane 2 is a plasmid control, Lane 3 is a 1:5 metal complex/base pair mixture of the plasmid with the metal complex incubated at 37° C. for 20 minutes, Lane 4 is a 1:5 metal complex/base pair mixture of the plasmid with the metal complex photolyzed at >475 nm for 20 minutes. B, DNA Photocleavage of pBluescript using [{(tpy)RuCl (dpp)}$_2$RhCl$_2$](PF$_6$)$_3$:Lane 1 is the λ molecular weight standard, Lane 2 is a plasmid control, Lane 3 is a 1:5 metal complex/base pair mixture of the plasmid with the metal complex incubated at 37° C. for 20 minutes, Lane 4 is a 1:5 metal complex/base pair mixture of the plasmid with the metal complex photolyzed at >475 nm for 20 minutes. C, DNA Photocleavage of pUC18 using [{(tpy)RuCl(bpm)}$_2$RhCl$_2$](PF$_6$)$_3$:Lane 1 is the λ molecular weight standard, Lane 2 is a plasmid control, Lane 3 is the plasmid alone photolyzed λ>475 nm for 15 mins, Lane 4 is a 1:5 metal complex/base pair mixture of the plasmid with the metal complex incubated at 37° C. for 15 minutes, Lane 5 is a 1:5 metal complex/base pair mixture of the plasmid with the metal complex photolyzed at >475 nm for 15 minutes.

DETAILED DESCRIPTION OF THE PREFERRED EMBODIMENTS OF THE INVENTION

The present invention provides novel metallic DNA cleaving agents that exhibit unique supramolecular architecture. The agents are supramolecular metal complexes in which a novel type of excitation is used. In the complexes, charge is transferred from one metal to another to generate a metal-to-metal charge transfer state, a unique type of excited state for application to photoactivated DNA cleavage. The complexes are able to cleave DNA as a direct result of the molecular design which localizes the highest occupied molecular orbital on at least one charge transfer light absorbing metal center, and the lowest unoccupied molecular orbital on a bioactive electron accepting metal center. This general molecular architectural scheme allows great flexibility in terms of the design of DNA cleaving complexes since many different substances may function as components of the system. Further, in contrast to most known photodynamic therapy agents, the DNA cleaving agents of the present invention do not require oxygen to function. They thus function efficiently in intracellular environments where O$_2$ levels are low. Also, since these agents do not generate singlet oxygen, incidental damage to healthy tissue due to release of $^1$O$_2$ to the surrounding environment cannot occur. In addition, the complexes are activated by the application of visible, low energy light, thus precluding unwanted cellular damage (e.g. of healthy tissue) which occurs as a result of the use of high energy light.

In the agents, three essential components are coupled: 1) at least one metal to ligand charge transfer (MLCT) light absorbing metal center; 2) a bridging π-acceptor ligand; and 3) an electron acceptor metal center. The function of the metal to ligand charge transfer light absorber is to produce an initially optically populated metal to ligand charge transfer state. Requirements of the bridging π-acceptor ligand are that it must coordinate to both the light absorbing metal and the electron acceptor metal, and possess a π system capable of being involved in an initial metal to ligand charge transfer excitation. The requirement for the electron acceptor metal is that it bind to the bridging π-acceptor ligand and be energetically capable of accepting an electron from the optically populated MLCT state to produce the reactive metal to metal charge transfer (MMCT) state. Without being bound by theory, it is believed that it is the MMCT state that functions to cleave the DNA to which the complex is bound.

In one embodiment of the present invention, two metal to ligand charge transfer light absorbers are utilized. However, those of skill in the art will recognize that only one MLCT light absorber need be present in the complex of the present invention. Alternatively, more than two such light absorbers may be incorporated to produce the initially optically populated metal to ligand charge transfer state. The exact number and type of MLCT light absorbers used in the supramolecular metallic complexes of the present invention may vary, depending on several factors including but not limited to: the desired excitation wavelength to be employed; the oxidation potential of interest for the metal based highest occupied molecular orbital; the required extinction coefficient for the excitation wavelength; ease of synthesis of the complex; cost and/or availability of components; and the like. Any suitable number of MLCT light absorbers may be used so long as within the complex an initial optically populated MLCT state is produced upon exposure to light or radiant energy, and which can be relayed to a suitable bridging ligand for transfer to an electron acceptor metal. In preferred embodiments, the number of MLCT light absorbers will range from 1 to about 14, and preferably from 1 to about 5, and more preferably from 1 to about 3. In one embodiment of the invention, two MLCT light absorbers are utilized.

Those of skill in the art will recognize that many suitable metals exist that can function as MLCT light absorbers in the practice of the present invention. Examples include but are not limited to ruthenium(II), osmium(II), rhenium (I), iron (II), platinum(I), etc. In preferred embodiments, two ruthenium(II) or two osmium(II) centers are utilized.

The complexes of the present invention require the presence of at least one bridging π-acceptor ligand capable of being involved in an initial metal to ligand charge transfer excitation. By "bridging ligand" we mean that, in the supramolecular complex, the π-acceptor ligand is located or positioned (i.e. bonded, coordinated) between an MLCT light absorber and an electron acceptor metal. Further, if there is more than one MLCT light absorber in the complex, the bridging π-acceptor ligands will be positioned to attach each light absorbing unit to either another light absorbing unit or directly to the electron accepting metal center.

The π-acceptor ligands coordinate or bind to the metal centers via donor atoms. Those of skill in the art will recognize that many suitable substances exist which contain appropriate donor atoms and may thus function as π-acceptor ligands in the complexes of the present invention. These π-acceptor ligands fall into two categories, bridging and terminal ligands. Bridging ligands serve to connect metal centers and thus bind to or coordinate two separate metal centers. Terminal ligands bind or coordinate to only one metal center and serve to satisfy the needed coordination sphere for such metals and provide a means to tune both light absorbing and redox properties of that metal center. For example, substances with: nitrogen donor atoms (e.g. pyridine- and pyridimidine-containing moieties such as 2,2'-bipyridine ("bpy"); 2,2':6',2"-terpyridine ("tpy"); 2,3-bis(2-pyridyl)pyrazine ("dpp"); and 2,2'-bipyridimidine ("bpm"); 2,3-bis(2-pyridyl)quinoxaline; 2,3,5,6,-tetrakis(2-pyridyl) pyrazine; carbon and nitrogen donor atoms (e.g. 2,2'-phenylpyridine); phosphorus donor atoms (e.g. triphenylphosphine, diethylphenylphosphine); etc. In preferred embodiments of the present invention, the π-acceptor ligands are bpy, tpy, dpp and bpm.

Further, those of skill in the art will recognize that, depending on the number of available coordination sites on the metals to which the π-acceptor ligands are coordinated, other extraneous ligands may also be present to complete the coordination sphere of the metal. Examples of such ligands include but are not limited to halogens such as Cl and Br, COOH, CO, $H_2O$, $CH_3CN$, etc.

The electron acceptor metal is an essential component of this molecular design. Those of skill in the art will recognize that many metals may be used as the electron acceptor metal in the complexes of the present invention. Examples of suitable metals include but are not limited to rhodium(III), platinum(IV), cobalt(III), iridium(III). Any metal that can bind to a bridging π-acceptor ligand and accept an electron from the optically populated MLCT state to produce the reactive MMCT state may be utilized. In a preferred embodiment of the invention, the electron acceptor metal is rhodium(III). Further, the number of electron acceptor metal centers in the complex may also be varied. Multifunctional systems could be designed that use many electron acceptor sites to enhance the functioning of the system by providing additional bioactive sites within a single molecular architecture.

In general, the supramolecular architecture of the complexes of the present invention can be varied by changing the identity and number of components of the complex. However, it is necessary to retain the components in sufficiently close location and appropriate orientation to provide the necessary electronic coupling. This coupling is necessary to allow for electron transfer from the initial π-acceptor ligand, that accepts the charge in the initially populated metal to ligand charge transfer state, to the electron accepting metal center to lead to the formation of the reactive metal to metal charge transfer state. It is also important that component separation and orientation not allow for rapid relaxation of the reactive MMCT state, facilitated by rapid back electron transfer. Those of skill in the art will recognize that the precise distances between components and the orientation of the components will vary from complex to complex, depending on the identity of complex substituents. However, in general the distances will be confined to the multi-atomic or multi-angstrom scale.

Exemplary forms of the complexes of the invention contain two ruthenium- or osmiun-based light absorbers which are coupled to a biologically active rhodium metal site. In these embodiments, the light absorbing metal centers are occupied by Ru or Os, and the central electron acceptor metal site is occupied by Rh.

Preferred embodiments of the complexes include:

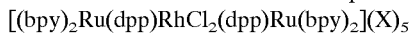
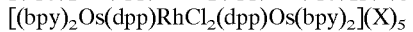
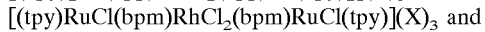 and
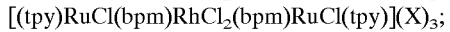;

where X is a counterion such as $PF_6^-$, $Cl^-$, $Br^-$, $CF_3SO_3^-$, $BF_4^-$, $ClO_4^-$, $SO_4^{2-}$, etc. Those of skill in the art will recognize that many such suitable counterions exist and may be utilized to form the salt form of a complex without altering the fundamental properties of the complex, other than its solubility.

The invention further provides new compositions of matter:

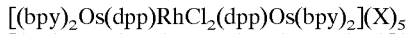
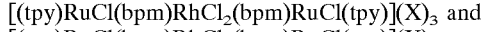 and
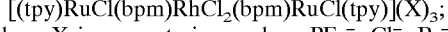;

where X is a counterion such as $PF_6^-$, $Cl^-$, $Br^-$, $CF_3SO_3^-$, $BF_4^-$, $ClO_4^-$, $SO_4^{2-}$, etc. as above.

The DNA cleaving agents of the present invention may be used for cleavage of DNA in many settings, including but not limited to cleavage of purified or partially purified DNA in laboratory setting for investigational purposes; and for the cleavage of DNA within cells, either ex vivo or in vivo. For example, ex vivo uses include cleavage of DNA in cultured cells for any reason, or of cells that have been removed from an individual with the intent of reintroducing the cells into the individual (or another individual) after manipulation of the cells (e.g. purging of tumor cells, genetic engineering of the cells, etc.) and the like. Examples of in vivo uses include the cleavage of DNA of cells within an organism, especially unwanted hyperproliferating cells such as tumor or cancer cells (including but are not limited to leukemia cells, ovarian cancer cells, Burkitt's lymphoma cells, breast cancer cells, gastric cancer cells, testicular cancer cells, and the like), and cells associated with psoriasis, warts, macular degeneration and other non-malignant hyperproliferating conditions.

While the method of the present invention is principally intended to thwart replication of hyperproliferating cells, other cellular populations may be targeted as well. For example, cells infected by a pathological agent such as a virus or bacterium, may also be targeted.

Exposure of DNA to the agents of the present invention results in binding of the agents to the DNA and subsequent cleavage of the DNA. The cleavage pattern may be random. Alternatively, the complexes of the present invention may be purposefully designed to favor binding at particular regions of the DNA and so affect site specific (or at least site-preferential) cleavage. For example, the complexes may be designed to bind preferentially to a particular sequence of bases, or to a particular structural motif or location (e.g. to A-, B-, or Z-DNA, or to the major or minor groove). It is also possible to append to this supramolecular structure architecture recognition sites that would lead to site specific cleavage of DNA. For example, single stranded DNA sequences can be appended to the complexes to allow recognition of complementary strands and subsequent selective cleavage at the site of metal complex attachment. Further, proteins or fragments of proteins that bind selectively to specific regions of a DNA molecule may also be attached, e.g. topoisomerases, gyrases, DNA polymerases, etc. Methods of attaching or appending additional substituents to the complexes of the present invention would be well-known to those of skill in the art, e.g. by substitution of a non-essential ligand such as a terminal ligand. The complexes may be used to cleave either double- or single-stranded DNA, as well as DNA-RNA hybrids, and double- or single-stranded RNA.

In preferred embodiments, the agents of the present invention bind to and cleave DNA within cells for which it is desired to attenuate the ability to replicate. Without being bound by theory, the agents of the present invention appear to provide a less drastic mode of treating pathological conditions which result from the hyperproliferation of cells in that the agents appear to cause a cessation of replication without killing the hyperproliferating cells outright. This is an advantage because the immediate killing of, for example, all tumor cells in a tumor mass can have unwanted results for a patient in which the tumor is being treated. If millions of tumor cells are killed outright many or most of the cells undergo lysis, releasing their contents into the environment. The result of such a massive release of the contents of dead cells into an area of the body can generate, for example, inflammatory and other unwanted reactions in otherwise healthy tissue in the environment. By biasing the effects of the agent to a cessation of replication, the progression of the tumor is halted, and the tumor cells will relatively gradually undergo cell death. Thus, the body of the patient under treatment experiences less drastic treatment consequences. However, those of skill in the art will recognize that some cells in the hyperproliferating tissue may also be killed outright by exposure to the DNA cleaving agents of the present invention. Other potential benefits could include attenuation of the cancer cells that would make them more susceptible to other types of cell killing such as chemotherapy or radiotherapy. Indeed, the methods of the instant invention may be practiced in conjunction with other such therapeutic measures.

The present invention provides specificity in attenuating cellular proliferation in that activation of DNA cleavage and subsequent cell damage and/or death will occur only when the cells containing the cleavage agent are exposed to suitable wavelengths of light. Suitable wavelengths of light for use in the practice of the present invention are dependent on the components of a given supramolecular complex. In general, low energy, visible light is utilized. By "low energy, visible light" we mean light of wavelengths >475 nm. For example, the wavelength used will depend on the complex of interest and its ability to absorb at that wavelength as well as the ability of the wavelength of light to penetrate the applicable biological material. Typically excitation would occur in the region of the intense metal to ligand charge transfer excitation. For example, for the system $[\{(bpy)_2Ru(dpp)\}_2RhCl_2](PF_6)_5$ the lowest lying such MLCT transition center is at 514 nm so optimal excitation would occur in this region (±about 50 nm) i.e. from about 464 to about 564 nm. However, those of skill in the art will recognize that other excitations further from the optimum can also be used due to the efficient internal conversion within supramolecular complexes of the type described herein. For example, for the system $[\{(bpy)_2Ru(dpp)\}_2RhCl_2](PF_6)_5$ excitation is possible throughout the UV and into the visible region, i.e. from about 200 to 650 nm. Light for in vivo applications where significant penetration is needed would typically be in the therapeutic window of about 650 to about 950 nm.

Specificity also results in that, when the targeted cells are in vivo (i.e. located internally within an organism), they will be exposed to light only when light of an appropriate wavelength is deliberately introduced into the environment, for example, during a studied surgical procedure using, e.g., optical fibers. For endoscopic use, optical fibers are threaded through a catheter or endoscope, allowing for small incisions while delivering a focused beam of light. When the targeted cells are ex vivo, cells are shielded until light of the wavelength that would activate the photosensitizing agent could be purposefully administered. Many companies (such as Coherent Medical Group, Coherent Inc., Palo Alto, Calif.), manufacture products specifically designed for the production of narrow wavelengths of light required for medical use. Those of skill in the art are acquainted with and will recognize that many such products exist. For example, gas lasers as well as LEDs are commercially available and capable of producing the requisite light. Any appropriate means of illuminating the target cells that results in activation of the photosensitizer molecule within the target cells, so that injury or death of the target cells results, may be utilized in the practice of the present invention. For example, of such methods of illumination, see Bellnier, D. et al. 1999. Design and construction of a light-delivery system for photodynamic therapy. *Med. Phys.* 26: 1552.

Specificity may also be conferred by the attachment to the complex of moieties which serve to direct the complex to a desired target. The agents may be coupled to targeting moieties such as antibodies, lectins, targeting fragments such as bacterial toxin molecules or fragments of such molecules, all of which can serve to direct the cleaving agent to the targeted population of cells, and also to promote uptake of the complex by the cell. For example, by coupling a DNA cleaving agent of the present invention to an antibody specific for an antigen that is expressed on a particular type of tumor cell, the agent can be delivered to the tumor cells of interest. See, for example, U.S. Pat. No. 6,426,400 to Zalutsky (Jul. 30, 2002) and U.S. Pat. No. 6,492,123 to Hollinger et al., (Dec. 10, 2002), the complete contents of which are hereby incorporated by reference.

Delivery of the DNA cleaving agents of the present invention to the DNA to be cleaved may be carried out by any of several known methods and will vary from case to case, depending on the particular application. For example, for some laboratory applications, solutions of the agents may be mixed directly with the DNA to be cleaved. For the cleavage of cultured cells (including ex vivo cells) the cleaving agents of the present invention may be added directly to the culture media where they are taken up by the cells. For in vivo applications, those of skill in the art will recognize that many means of administration exist, including but not limited to: direct application of the DNA cleaving agent in a suitable carrier, e.g. by topical administration to a cancerous lesion such as a melanoma or other area of exposed hyperproliferating tissue; or by delivery directly into the tumor or other hyperproliferating tissue, e.g. by injection or other type of direct infusion. Other means of delivery include systemic delivery. In the case of systemic delivery, many cells will be exposed to and internalize the agents of the present invention. However, only those cells which are later exposed to suitable wavelengths of light will be effected by the presence of the agent by cleavage of their DNA. Residual agent within non-targeted cells will be eliminated from the body over a time period of about two weeks, during which the patient must avoid exposure to wavelengths of light that would activate the agents.

Thus, the agents of the present invention may be administered by any of several suitable means that are well-known to those of skill in the art. For example, intramuscularly, intravenously, intratumorally, orally (e.g. in liquid or tablet/capusular form), via suppositories, via inhalation, and the like.

In order to effect administration of the agents of the present invention, the present invention also provides a composition for administration to hyperproliferating cells. The composition comprises at least one of the DNA cleaving agents and a suitable carrier, e.g. a suitable physiological carrier for in vivo administration, e.g. saline. The composition may be administered in any of a variety of suitable forms, including forms that include additional components such as buffers, stabilizers, nutrients, anti-oxidants, flavorings, colorants, and the like, which are appropriate to a means of administration. Those of skill in the art will recognize that the exact form will vary from application to application. The compounds can be administered in the pure form or in a pharmaceutically acceptable formulation including suitable elixirs, binders, and the like or as pharmaceutically acceptable salts or other derivatives. It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Solid diluents and excipients include lactose, starch, conventional disintergrating agents, coatings and the like. Preservatives such as methyl paraben or benzalkium chloride may also be used. Depending on the formulation, it is expected that the active composition will consist of 1–99% of the composition and the vehicular "carrier" will constitute 1–99% of the composition.

Likewise, the dosage, frequency and timing of administration will vary from case to case and will depend on factors such as the particular application, the nature and stage of a condition resulting from hyperproliferation of cells (e.g. size and location of a malignant or non-malignant tumor), characteristics of the patient (e.g. overall health, age, weight, gender and the like), and other factors such as ancillary treatments (chemotherapy, radiotherapy, and the like). The details of administration are best determined by a skilled practitioner such as a physician. Further, the details of administration are normally worked out during clinical trials. However, the approximate dosage range will preferably be from about 0.1 to 10 mg of agent per kg of weight, and more preferably from about 0.25 to 1.0 mg/kg. When treating DNA directly, the amount of agent to be administered is preferably in the range of about 0.1–50 µg per about 0.1–50 fig of DNA, and more preferably, in the range of about 1–10 µg per about 1–10 fig of DNA. Those of skill in the art will recognize that the precise amounts will vary depending, for example, on the precise characteristics of the complex and the DNA itself, on temperature, pH, and the like. Typically, the agent will be administered about 1 to 24 hours prior to exposure to a suitable light source, and preferably from about 1 to 4 hours prior to exposure to the light source.

Likewise, the dose or frequency of illumination of the target cells will vary from case to case, but will generally be in the range of 25–200 J/cm$^2$ light dose, 25–200 mW/cm$^2$ fluence rate (see Ochsner, M. 1997. Photodynamic Therapy: the Clinical Perspective. Review on applications for control of diverse tumours and non-tumour diseases. *Drug Res.*, 47:1185–1194).

Further non-limiting embodiments of the invention are presented in the following Examples section.

EXAMPLES

Background for Examples 1 to 4

Interest in the area of supramolecular chemistry has resulted in the design of many photochemically and electrochemically active ruthenium(II) polypyridyl complexes.[1-17] Supramolecular complexes have been designed, taking advantage of the long-lived metal-to-ligand charge transfer (MLCT) excited state of the widely studied [Ru(bpy)$_3$]$^{2+}$ chromophore,[1-3] focused on their use as photochemical molecular devices[4-9] (bpy) 2,2'-bipyridine. Incorporation of ruthenium(II) polypyridyl groups into a supramolecular motif eliminates the need for molecular collision resulting in facile electron or energy transfer. The bridge, which links the metal centers in these supramolecular complexes, is often a multidentate polyazine ligand.[4-17]

Figure 1B:
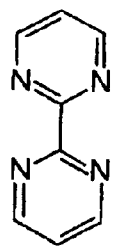

Polymetallic complexes incorporating polyazine bridging ligands (BL) have received a great deal of attention.[4-17] The BL serves to bring the metal centers into close proximity and creates a pathway for energy or electron transfer. The commonly used bridging ligand 2,3-bis(2-pyridyl)pyrazine (dpp) (FIG. 1A) binds to two metal centers through a pyridyl and a pyrazine nitrogen, acting as an AB chelate, resulting in a mixture of stereoisomers not typically separated.[4-9,12,14,15] Another BL which performs the same function but has not received as much attention is 2,2'-bipyrimidine (bpm) (FIG. 1B), which binds to two metal centers through two equivalent nitrogens eliminating the stereoisomers associated with the AB chelates.[11,13,16,17]

Figure 1C:
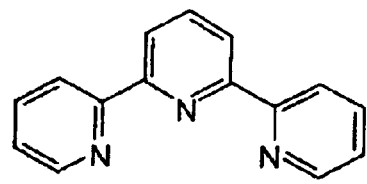

Within a supramolecular architecture, terminal ligands (TL), typically bpy, are coordinated to the ruthenium light absorbers. Another TL used in supramolecular complexes is 2,2':6',2"-terpyridine (tpy) (FIG. 1C). Although [Ru(tpy)$_2$]$^{2+}$ has a short-lived excited state,[18-20] the tpy ligand brings the advantage of eliminating the Λ and Δ isomeric mixtures associated with the tris-bidentate metal centers giving some stereochemical control in supramolecular complexes. Long lived excited states are observed for many ruthenium tpy complexes incorporating polyazine bridging ligands.[21-30]

Trimetallic complexes of the form [{(bpy)$_2$Ru(BL)}$_2$MCl$_2$]$^{5+}$, where BL=dpp, 2,3-bis(2-pyridyl)quinoxaline (dpq), and 2,3-bis(2-pyridyl)benzoquinoxaline (dpb) and M=Ir(III),[31-33] have been studied, and a preliminary report of M=Rh(III) has appeared.[32b] The system with M=Ir and BL=dpb acts as a molecular device for photoinitiated electron collection[31a] and is an electrocatalyst for $CO_2$ reduction.[33] The bpm trimetallic complexes [{(bpy)$_2$Ru(bpm)}$_2$IrCl$_2$]$^{5+}$ and [{(bpy)$_2$Ru(bpm)}$_2$RhCl$_2$]$^{5+}$ have Ru-(dπ) based highest occupied molecular orbitals (HOMOs) and bridging ligand, bpm(π*), based lowest unoccupied molecular orbitals (LUMOs).[34]

A number of important studies on the coupling of ruthenium light absorbers to rhodium electron acceptors in supramolecular frameworks have appeared.[32,34-44] Interesting systems with varying bridge length were studied by Indelli, Scandola, Collin, Sauvage, and Sour, [(tpy)Ru(tpy(Ph)$_n$tpy)Rh(tpy)]$^{5+}$ (n=0, 1, or 2).[36] Linked bpy systems of the type [(Me$_2$phen)$_2$Ru$^{II}$(Mebpy-CH$_2$CH$_2$-Mebpy)Rh$^{III}$(Mebpy)$_2$]$^{5+ \ 36,37}$ and a dpp bridged system [(bpy)$_2$Ru$^{II}$(dpp)Rh$^{III}$(bpy)$_2$]$^{5+ \ 35}$ have been investigated. Endicott et al. have studied Ru$^{II}$,Rh$^{III}$ cyanide-bridged complexes.[41] Often these systems are reported to undergo intramolecular electron-transfer quenching of the Ru-based MLCT excited state by the rhodium center.

A trimetallic structural motif would be an interesting framework to exploit the electron acceptor properties of the rhodium metal center. This requires the development of synthetic methods and the ability to modulate orbital energies in a supramolecular architecture. Within this framework the trimetallic complexes [{(tpy)RuCl(dpp)}$_2$RhCl$_2$](PF$_6$)$_3$ and [{(tpy)RuCl(bpm)}$_2$RhCl$_2$](PF$_6$)$_3$ have been synthesized and characterized by FAB mass spectral analysis, electronic absorption spectroscopy, electrochemistry, and spectroelectrochemistry. These complexes couple two ruthenium light absorbers (LA) to a central electron collecting (EC) rhodium metal center to form a LA-BL-EC-BL-LA assembly. The interesting effects of bridging ligand and terminal ligands on the spectroscopic and electrochemical properties of these complexes is discussed.

Material and Methods for Examples 1 to 4

Materials 2,2':6',6"-Terpyridine (tpy) (GFS chemicals), ruthenium(III) chloride hydrate, rhodium trichloride hydrate, and 2,2'-bipyrimidine (bpm) (Alfa), triethylamine (Acros), 2,3-bis(2-pyridyl)-pyrazine (dpp) (Aldrich), (80–200 mesh) adsorption alumina (Fisher), and spectroquality grade acetonitrile and toluene (Burdick and Jackson) were used as received. Tetrabutylammonium hexafluorophosphate Bu$_4$NPF$_6$ (used as supporting electrolyte for electrochemistry experiments) was prepared by the aqueous metathesis of tetrabutylammonium bromide (Aldrich) with potassium hexafluorophosphate (Aldrich). After several recrystallizations from ethanol the white crystals were dried under vacuum and stored in a vacuum desiccator. Elemental analysis was performed by Galbraith Laboratories, Inc., Knoxville, Tenn.

Synthesis (tpy)RuCl$_3$,[45] [(tpy)RuCl(dpp)](PF$_6$),[46] [(tpy)RuCl(bpm)](PF$_6$),[47] [{(bpy)$_2$Ru(dpp)}$_2$RhCl$_2$](PF$_6$)$_5$,[32b] and [{(bpy)$_2$Ru(bpm)}$_2$RhCl$_2$](PF$_6$)$_5$[34] were synthesized as described previously.

[{(tpy)RuCl(dpp)}$_2$RhCl$_2$](PF$_6$)$_3$

A solution of 0.40 g (0.54 mmol) of [(tpy)RuCl(dpp)](PF$_6$) and 0.080 g (0.36 mmol) of rhodium trichloride hydrate in 2:1 EtOH/H$_2$O was heated at reflux for 1 h. After being cooled to room temperature, the reaction mixture was added dropwise to an aqueous solution of 100 mL of H$_2$O and 100 mL of saturated KPF$_6$(aq) solution with stirring. The resulting precipitate was filtered, washed with 30 mL of cold water and 30 mL of cold ethanol followed by 30 mL of ether, and air-dried for 30 min. The product was dissolved in a minimum amount of acetonitrile (ca. 5 mL), flash precipitated in 200 mL of ether, and collected by vacuum filtration to yield a purple powder (0.40 g, 0.22 mmol, 82% yield). Anal. Calcd for [{(tpy)RuCl(dpp)}$_2$RhCl$_2$](PF$_6$)$_3$,8H$_2$O; C, 35.52; H, 2.98; N, 10.00. Found: C, 35.20; H, 2.35; N, 9.93. UV/vis (CH$_3$CN): $\lambda$max (nm) [$\epsilon \times 10^{-4}$ M$^{-1}$ cm$^{-1}$]) 274 [4.70], 314 [6.48], 360 (sh) [2.72], 460 [1.13], 540 [2.72]. FAB-MS ion (m/z; relative abundance): [{(tpy)RuCl(dpp)}$_2$RhCl$_2$](PF$_6$)$_2$$^+$(1673, 100); [{(tpy)RuCl(dpp)}$_2$RhCl](PF$_6$)$_2$$^+$(1636, 10); [{(tpy)RuCl(dpp)}$_2$RhCl$_2$](PF$_6$)$^+$(1527, 25); [{(tpy)RuCl(dpp)}$_2$RhCl](PF$_6$)$^+$(1493, 10).

[{(tpy)RuCl(bpm)}$_2$RhCl$_2$](PF$_6$)$_3$

A solution of 0.32 g (0.49 mmol) of [(tpy)RuCl(bpm)](PF$_6$) and 0.070 g (0.32 mmol) of rhodium trichloride hydrate in 2:1 EtOH/H$_2$O was heated at reflux for 2 h. After the reaction mixture was cooled to room temperature, a black residue was removed by filtration. The filtrate was added dropwise to an aqueous solution of 100 mL of H$_2$O and 100 mL of saturated KPF$_6$(aq) solution with stirring. A brown precipitate formed, which was filtered and washed with 30 mL of cold ethanol followed by 30 mL of ether. The resulting brown product was dissolved in a minimum of acetonitrile (ca. 5 mL), flash precipitated in 200 mL of ether, and collected by vacuum filtration to yield a greenish/brown powder (0.28 g, 0.17 mmol, 72% yield). Anal. Calcd for [{(tpy)RuCl(bpm)}$_2$RhCl$_2$](PF$_6$)$_3$,CH$_3$CN,H$_2$O; C, 33.45; H, 2.28; N, 12.19. Found: C, 33.33; H, 2.40; N, 11.76. UV/vis (CH$_3$CN): $\lambda$max (run) [$\epsilon \times 10^{-4}$M$^{-1}$ cm$^{-1}$]) 272 [6.21], 312 [5.50], 330 (sh) [3.11], 464 [2.50], 656 [1.00]. FAB-MS ion (m/z; relative abundance): [{(tpy)RuCl(bpm)}$_2$RhCl$_2$](PF$_6$)$_2$+(1520, 85); [{(tpy)RuCl(bpm)}$_2$RhCl](PF$_6$)$_2$$^+$(1485, 15); [{(tpy)RuCl(bpm)}$_2$RhCl$_2$](PF$_6$)$^+$(1375, 100); [{(tpy)RuCl(dpp)}$_2$RhCl](PF$_6$)+(1340, 20).

Electronic Spectroscopy

Electronic absorption spectra were recorded at room temperature using a Hewlett-Packard 8452 diode array spectrophotometer with 2 nm resolution. Samples were run at room temperature in Burdick and Jackson UV-grade acetonitrile in 1 cm quartz cuvettes.

Electrochemistry

Cyclic voltammograms were recorded using a one-compartment three-electrode cell, Bioanalytical Systems (BAS), equipped with a platinum wire auxiliary electrode. The working electrode was a 1.9 mm diameter glassy carbon disk from BAS. Potentials were referenced to a Ag/AgCl electrode (0.29 V vs NHE), which was calibrated against the FeCp$_2$/FeCp$_2$$^+$ redox couple (0.67 V vs NHE).48 The supporting electrolyte was 0.1 M Bu$_4$NPF$_6$, and the measurements were made in Burdick and Jackson UV-grade acetonitrile, which was dried over 3 Å molecular sieves.

Spectroelectrochemistry

Spectroelectrochemical measurements were conducted according to a previously described method using a locally constructed H-cell which uses a quartz cuvette as the working compartment.49 The working and auxiliary compartments were separated by a fine porous glass frit. The working electrode and auxiliary electrodes were high surface area platinum mesh, and the reference electrode was Ag/AgCl (0.29 V vs NHE). The measurements were made in 0.1 M Bu$_4$NPF$_6$/acetonitrile solutions that were 2×10$^{-5}$ M metal complex. The electrolysis potential was controlled by a BAS 100W electrochemical analyzer.

FAB Mass Spectrometry

FAB mass spectral analysis was performed by M-Scan Incorporated, West Chester, Pa., on a VG Analytical ZAB 2-SE high-field mass spectrometer using m-nitrobenzyl alcohol as a matrix. The trimetallic gave very nice FABMS patterns with sequential loss of each PF$_6$ ion being observed. The fragmentation pattern was consistent with the proposed molecular structure.

Example 1

Synthesis

Figure 2:
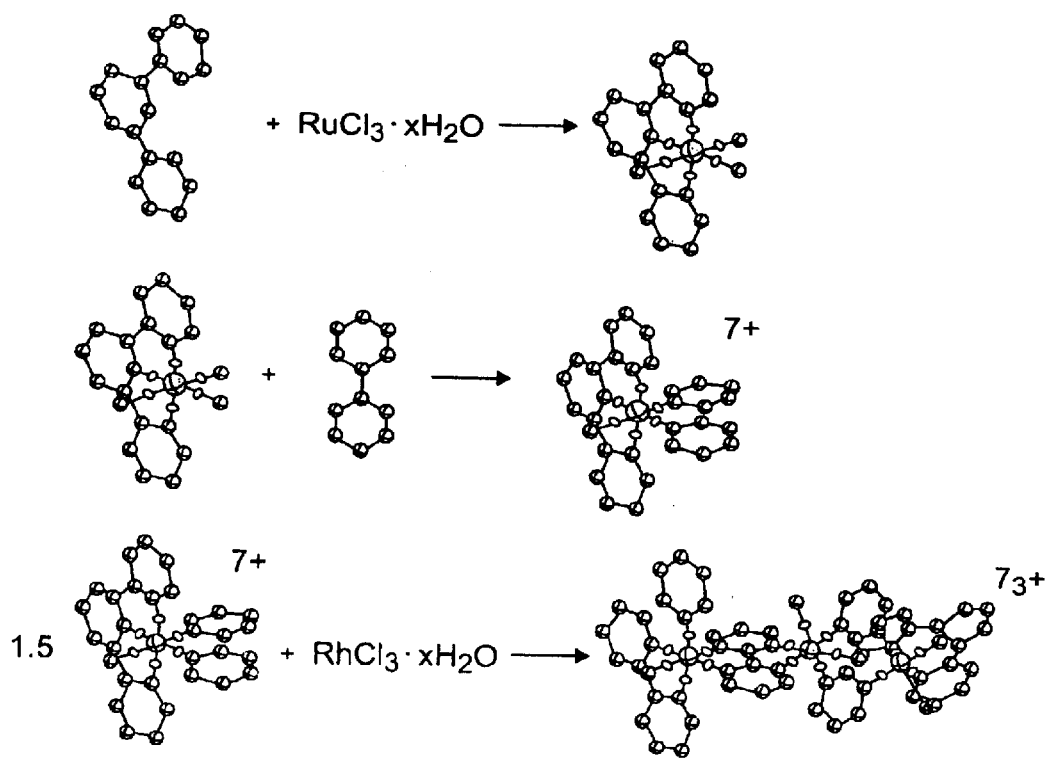
FIG. 2. Schematic of building-block synthesis of [{(tpy)RuCl(bpm)}$_2$RhCl$_2$]$^{3+}$.

The supramolecular complexes [{(tpy)RuCl(dpp)}$_2$RhCl$_2$](PF$_6$)$_3$ and [{(tpy)RuCl(bpm)}$_2$RhCl$_2$](PF$_6$)$_3$ were prepared in good yields under mild conditions using a building-block approach. It is this method that allows for easy variation of structural components within this structural motif. The tpy is first bound to ruthenium followed by BL attachment.[45,46] The trimetallic complexes are assembled by reaction of the [(tpy)RuCl(BL)](PF$_6$), where BL=dpp or bpm, with a slight excess of rhodium(III) trichloride hydrate. The synthesis of [{(tpy)RuCl(bpm)}$_2$RhCl$_2$](PF$_6$)$_3$ by this method is illustrated in FIG. 2. This method of binding the bpm or dpp ligand to the ruthenium metal center first and then binding to the rhodium metal center yields clean reactions with easily purified products. The use of excess rhodium(III) trichloride hydrate ensures that most of the monometallic precursor is reacted. The major product in each case is the desired trimetallic. The excess rhodium(III) trichloride is easily removed by aqueous washings of the precipitated hexafluorophosphate salt of the trimetallic complex The use of dpp as a bridging ligand leads to cis and trans type stereoisomers, around the Ru which are not detectable by cyclic voltammetry or electronic absorption spectroscopy.[46,47] Utilization of the symmetric bridging ligand bpm eliminates the cis/trans type stereoisomers present in the dpp synthons.

These trimetallic complexes were effectively characterized by FAB mass spectral analysis. These supramolecular complexes typically show high mass peaks that are easy to interpret with loss of counterions and intact ligands. Fragmentation patterns for these trimetallics show sequential loss of PF$_6$$^-$ counterions and the chlorides bound to the rhodium center.

This example demonstrates that a method has been developed to prepare such complexes that is general and allows for component modification and that the described complexes have the proposed formulation.

Example 2

Electrochemistry

Trimetallic complexes of the form [{(bpy)$_2$Ru(CL)}$_2$RhCl$_2$]$^{5+}$ are characterized by reversible ruthenium oxidations, irreversible rhodium reductions, and reversible ligand reductions, with the BLs (dpp or bpm) being reduced prior to the bpy ligands.[32,34] They display a Ru(dσ) HOMO. The LUMO is localized on Rh(dσ*) for dpp and bpm(π*) for the bpm bridged system.

Figure 4A:
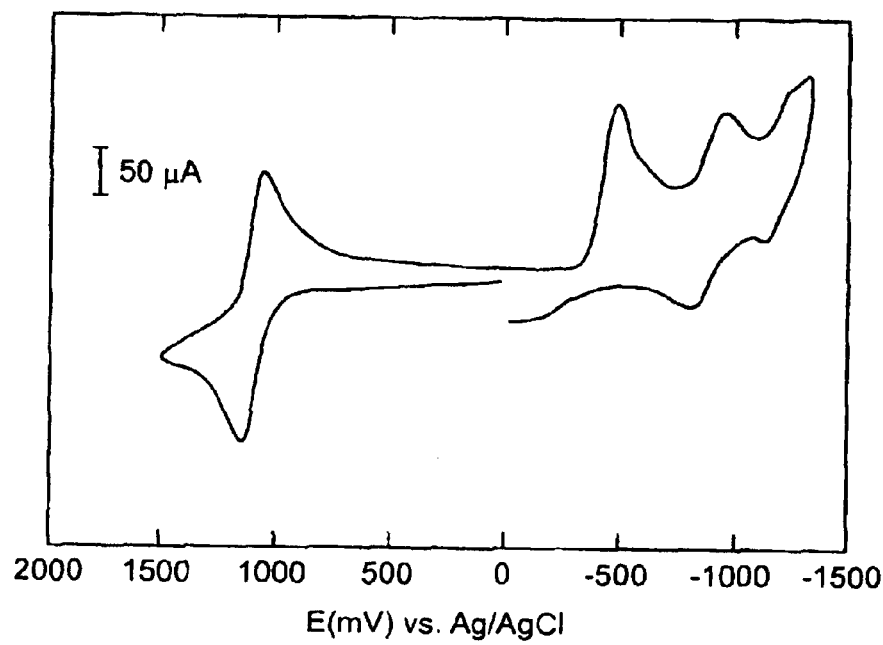
FIG. 4A and B. Cyclic voltammograms of the trimetallic complexes [{(tpy)-RuCl(BL)}$_2$RhCl$_2$](PF$_6$)$_3$ in 0.4 M Bu$_4$NPF$_6$ in CH$_3$CN, where BL=2,3-bis(2-pyridyl)pyrazine, dpp (A), or 2,2'-bipyrimidine, bpm (B), and tpy=2,2':6',2"-terpyridine. Potentials recorded vs Ag/AgCl reference electrode (0.29 V vs NHE).

The cyclic voltammogram of $[\{(tpy)RuCl(dpp)\}_2RhCl_2]^{3+}$ in 0.4 M $Bu_4NPF_6/CH_3CN$ solution is illustrated in FIG. 4A and summarized in Table 1.

TABLE 1

Electrochemical Properties for a Series of Ru(II) and Ru(II)/Rh(III)/Ru(II) Trimetallic Complexes Where tpy = 2,2':6',2''-Terpyridine, dpp = 2,Bis(2-pyridyl)pyrazine, and bpm = 2,2'-Bipyrimidine

| $E_{1/2}$ in V[a] ($\Delta E_p$ in mV) | assigment |
|---|---|
| $[\{(tpy)RuCl(dpp)\}_2RhCl_2](PF_6)_3$ | |
| 1.12 (85) | $2Ru^{III/II}$ |
| $E_p^c = 0.47$ | $Rh^{III/I}$ |
| −0.87 (140) | $dpp,dpp/dpp,dpp^-$ |
| −1.20 (95) | $dpp,dpp^-/dpp^-,dpp^-$ |
| $[\{(tpy)RuCl(bpm)\}_2RhCl_2](PF_6)_3$ | |
| 1.12 (100) | $2Ru^{III/II}$ |
| $E_p^c = 0.26$ | $Rh^{III/I}$ |
| $E_p^c = 0.38$ | $Rh^{II/I}$ |
| −0.70 (100) | $bpm,bpm/bpm,bpm^-$ |
| −1.12 (115) | $bpm,bpm^-/bpm^-,bpm^-$ |
| $[\{(bpy)_2Ru(dpp)\}_2RhCl_2](PF_6)_5^{32b}$ | |
| 1.6 | $2Ru^{III/II}$ |
| $E_p^c = -0.39$ | $Rh^{III/I}$ |
| −0.79 | $dpp,dpp/dpp,dpp^-$ |
| −1.02 | $dpp,dpp^-/dpp^-,dpp^-$ |
| $[\{(bpy)_2Ru(bpm)\}_2RhCl_2](PF_6)_5^{34}$ | |
| 1.7 | $2Ru^{III/II}$ |
| −0.13 | $bpm,bpm/bpm,bpm^-$ |
| −0.26 | $bpm,bpm^-/bpm^-,bpm^-$ |
| −0.78 | $Rh^{III/I}$ |
| $[(tpy)RuCl(dpp)](PF_6)^{47}$ | |
| 1 | $Ru^{III/II}$ |
| −1.21 | $dpp^{0/-}$ |
| −1.54 | $tpy^{0/-}$ |
| $[(tpy)RuCl(bpm)](PF_6)^{47}$ | |
| 1.01 | $Ru^{III/II}$ |
| −1.15 | $bpm^{0/-}$ |
| −1.56 | $typ^{0/-}$ |

[a]Potentials reported versus the Ag/AgCl (0.29 V vs NHE) reference electrode in 0.1 M $Bu_4NPF_6CH_3CN$.

Figure 4B:
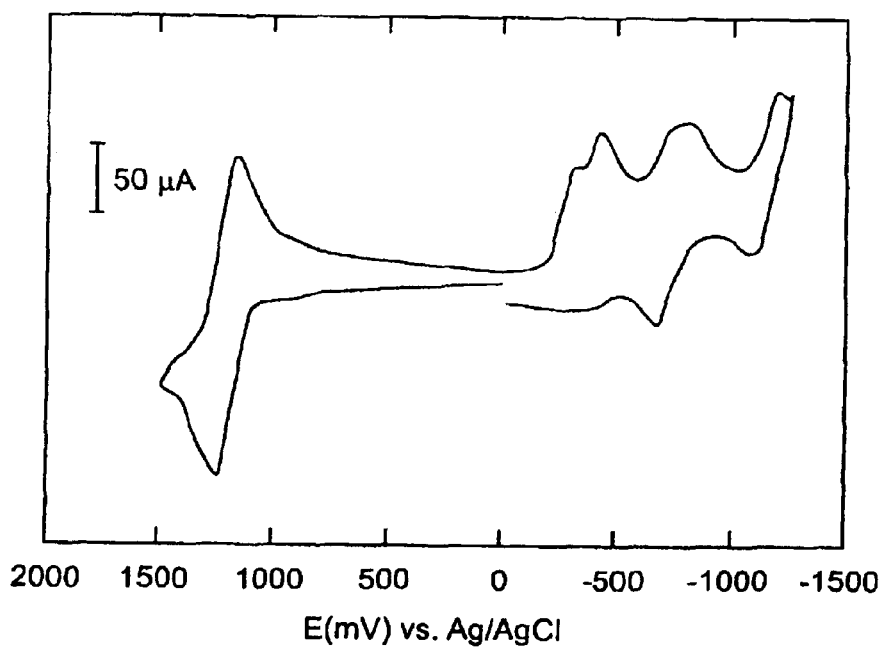
Figure 5:
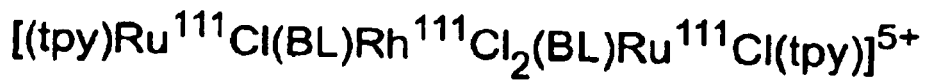
FIG. 5. Electrochemical Mechanism for the Ru,Rh,Ru Triads.
Figure 5:
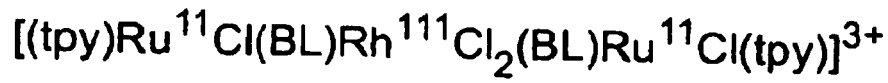

A reversible redox couple at 1.12 V is observed in the positive potential region. This redox couple is attributed to two overlapping $Ru^{II/III}$ oxidations. These LAs are largely electronically uncoupled, allowing them to function independently.[31,34] The $Ru^{II/III}$ couples occur 480 mV less positive in the $[\{(tpy)RuCl(dpp)\}_2RhCl_2]^{3+}$ systems relative to the bpy systems, resulting from the chloride coordination on the Ru centers in the tpy systems. Reductively an irreversible peak is observed at −0.47 V. This couple results from the overlapping reduction of the Rh(III) to Rh(II) and then to Rh(I). Similar behavior is reported by DeArmond for the $[Rh(bpy)_2Cl_2]^+$.[50] Reduction of the Rh(III) to Rh(I) should be followed by conversion of the formally $d^6$ pseudooctahedral Rh(III) to a square planar $d^8$ Rh(I). This occurs by chloride loss as evidenced by the presence of free chloride seen in anodic scans that follow cathodic scans through the $Rh^{III/I}$ couple. No evidence of Rh(I) reoxidation is seen in multiple scan experiments. Two quasi-reversible redox couples at −0.87 and −1.20 V are attributed to sequential reduction of the two equivalent dpp bridging ligands, dpp,dpp/dpp,dpp⁻ and dpp,dpp⁻/dpp⁻,dpp⁻, respectively. Further reductive scanning results in a neutral species leading to adsorption of the complex onto the electrode surface. $[\{(tpy)RuCl(dpp)\}_2RhCl_2]^{3+}$ exhibits a ruthenium(II) based HOMO and a rhodium(III) based LUMO, analogous to $[\{(bpy)_2Ru(dpp)\}_2RhCl_2]^{5+}$. The proposed electrochemical mechanism is shown in FIG. 5. The cyclic voltammogram of $[\{(tpy)RuCl(bpm)\}_2RhCl_2]^{3+}$ in 0.4 M $Bu_4NPF_6/CH_3CN$ solution is illustrated in FIG. 4B and summarized in Table 1. A single reversible oxidation wave is observed at $E_{1/2}=1.21$ V and is assigned to the two overlapping $Ru^{III/II}$ redox couples, indicating that the two ruthenium centers are largely electronically uncoupled. Two closely spaced irreversible reductions at −0.26 and −0.38 V in FIG. 4B are assigned as sequential one-electron reductions of the rhodium center, $Rh^{III/II}$ and $Rh^{II/I}$. Interestingly, when bpm is used as the BL these two couples shift apart relative to the dpp analogue, indicating some stability of the Rh(II) oxidation state. This is an unusual property for a $[Rh(NN)_2Cl_2]^+$ system. Reversing the scan after the $Rh^{III/II}$ couple but prior to the Rh $I^{II/I}$ couple does lead to the observation of a small return wave corresponding to Rh(II) reoxidation, but this couple remains largely irreversible. Further cathodic scanning past the $Rh^{II/I}$ couple reveals the sequential one-electron reduction of the bpm bridging ligands, bpm,bpm/bpm,bpm⁻ and bpm,bpm⁻/bpm⁻,bpm⁻. Further reduction leads to adsorption.

Figure 3A:
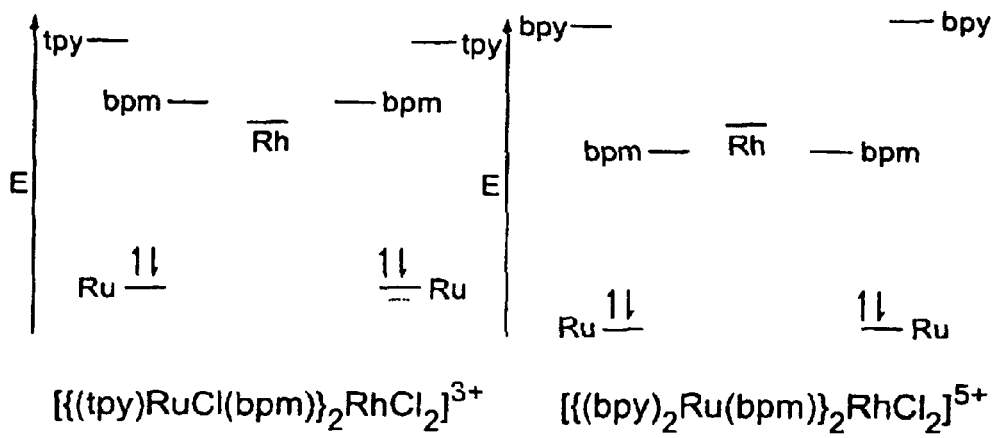
FIGS. 3A and B. A, Orbital Energy Diagram for [{(tpy)RuCl(bpm)}$_2$RhCl$_2$]$^{3+}$ and [{(bpy)$_2$Ru(bpm)}$_2$RhCl$_2$]$^{5+}$; B, Orbital Energy Diagram for [{(tpy)RuCl(dpp)}$_2$RhCl$_2$]$^{3+}$ and [{(bpy)$_2$Ru(dpp)}$_2$RhCl$_2$]$^{5+}$.
Figure 3B:
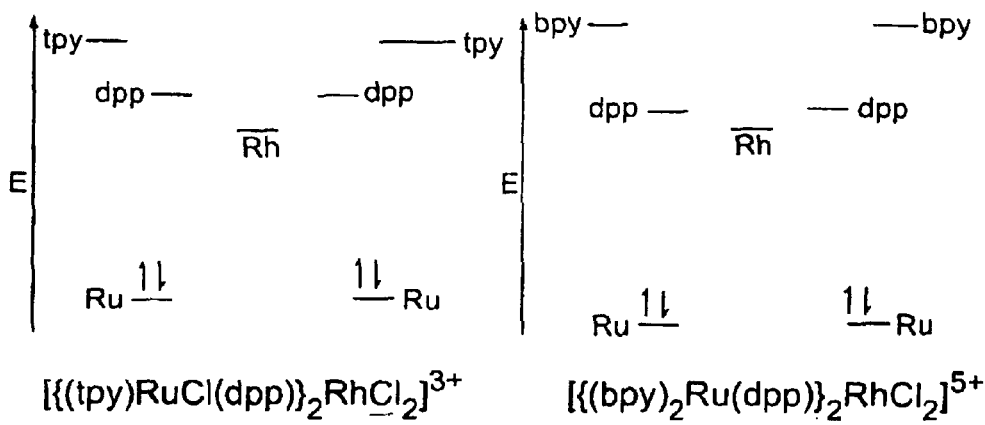

The new bpm-based trimetallic complex $[\{(tpy)RuCl(bpm)\}_2RhCl_2]^{3+}$ displays a Rh(dσ*) LUMO in marked contrast to the bpm(π*) LUMO in $[\{(bpy)_2Ru(bpm)\}_2RhCl_2]^{5+}$. The redox chemistry of $[\{(bpy)_2Ru(bpm)\}_2RhCl_2]^{5+}$ is characterized by two reversible one-electron bpm-based reductions at −0.13 and −0.26 V followed by the irreversible reduction of the rhodium center, $Rh^{III/I}$ at −0.78 V.[34] Variation of the terminal ligands on the Ru metals indirectly modulates the energy of the bpm ligand orbitals. Coordination of the Cl⁻ ligand to ruthenium in $[\{(tpy)RuCl(bpm)\}_2RhCl_2]^{3+}$ results in a more electron rich Ru center. This leads to less stabilization of the bpm(π*) orbitals relative to the bis-bpy analogue. As the bpm(π*) and Rh(dσ*) orbitals are very close in energy, this modulation of the bpm(π*) orbital energies by terminal ligand variation leads to orbital inversion, FIGS. 3A and 3B.

This electrochemical data indicates that, in the trimetallic complexes $[\{(tpy)RuCl(BL)\}_2RhCl_2]^{3+}$ and $[\{(bpy)_2Ru(BL)_2RhCl_2]^{5+}$, the BL(π*) and Rh(dσ*) orbitals are close in energy. In all cases the HOMO is localized on the Ru(dπ) orbitals. The localization of the LUMO can be modulated, being Rh(dσ*) in nature for $[\{(tpy)RuCl(BL)\}_2RhCl_2]^{3+}$ (BL=dpp or bpm) and $[\{(bpy)_2Ru(dpp)\}_2RhCl_2]^{5+}$ and bpm (π*) in nature for $[\{(bpy)_2Ru(bpm)\}_2RhCl_2]^{5+}$.

This example demonstrates that the complexes display redox patterns consistent with their formulation. Additionally, the systems possess the necessary energetics to undergo the needed metal to ligand charge transfer excitation followed by intramolecular electron transfer to produce the desired reactive metal to metal charge transfer state.

Example 3
Electronic Absorption Spectroscopy

The electronic absorption spectral data in acetonitrile of the new trimetallic complexes, $[\{(tpy)RuCl(dpp)\}_2RhCl_2]^{3+}$ and $[\{(tpy)RuCl(bpm)\}_2RhCl_2]^{3+}$, as well as their monometallic precursors and trimetallic bpy analogues are assembled in Table 2. The UV regions of the spectra for all of these complexes show BL (dpp or bpm) and terminal ligand (tpy or bpy) π to π* transitions with the BLs expected to show the lowest lying π to π* bands.[1,4-9,34,47,51] The visible regions of the spectra are dominated by overlapping Ru(d π) to BL(π*) and Ru(d π) to bpy or tpy(π*) charge transfer (CT) transitions with BL based bands occurring at lower energy.

TABLE 2

Electronic Absorption Spectroscopy for a Series of Ru(II) and Ru(II)/Rh(III)/Ru(II) Trimetallic Complexes Where tpy = 2,2':6',2"-Terpyridine, dpp = 2,3-Bis(2-pyridyl)pyrazine, and bpm = 2,2'-Bipyrimidine[a]

| $\lambda_{max}$ (nm) | $\epsilon \times 10^{-4}$ (M$^{-1}$ cm$^{-1}$) | assignments |
|---|---|---|
| [{(tpy)RuCl(dpp)}$_2$RhCl$_2$](PF$_6$)$_3$ | | |
| 274 | 4.7 | tpy (π → π*) |
| 314 | 6.48 | tpy (π → π*) |
| 330(sh) | 5.41 | Ru(dπ) → tpy(π*) CT |
| 360(sh) | 2.72 | dpp (π → π*) |
| 460 | 1.13 | Ru(dπ) → tpy(π*) CT |
| 540 | 2.72 | Ru(dπ) → dpp(π*) CT |
| [{(tpy)RuCl(bpm)}$_2$RhCl$_2$](PF$_6$)$_3$ | | |
| 272 | 6.21 | tpy(π → π*) |
| 312 | 5.5 | tpy(π → π*) |
| 330(sh) | 3.11 | Ru(dπ) → tpy(π*) CT |
|  |  | bpm(π → π*) |
| 464 | 2.5 | Ru(dπ) → tpy(π*) CT |
|  |  | Ru(dπ) → bpm(π*) CT |
| 656 | 1 | Ru(dπ) → tpy(π*) CT |
| [{(bpy)$_2$Ru(dpp)}$_2$RhCl$_2$](PF$_6$)$_5$[b] | | |
| 242 | 6.53 | bpy(π → π*) |
| 284 | 9.64 | bpy(π → π*) |
| 344(sh) | 2.87 | dpp(π → π*) |
| 414 | 1.74 | Ru(dπ) → bpy(π*) CT |
| 514 | 2.01 | Ru(dπ) → dpp(π*) CT |
| [{(bpy)$_2$Ru(bpm)}$_2$RhCl$_2$](PF$_6$)$_5$[34] | | |
| 278 | 9 | bpy(π → π*) |
| 412 | 3.7 | Ru(dπ) → bpy(π*) CT |
|  |  | Ru(dπ) → bpm(π*) CT |
| 594 | 0.99 | Ru(dπ) → bpm(π*) CT |
| [(tpy)RuCl(dpp)](PF$_6$)[47] | | |
| 238 | 2.32 | dpp(π → π*) |
| 276 | 2 | tpy(π → π*) |
| 314 | 2.91 | tpy(π → π*) |
| 370 | 0.44 | Ru(dπ) → tpy(π*) CT |
| 514 | 0.89 | Ru(dπ) → tpy(π*) CT |
|  |  | Ru(dπ) → dpp(π*) CT |
| [(tpy)RuCl(bpm)](PF$_6$)[47] | | |
| 240 | 3.94 | bpm(π → π*) |
| 266 | 2.92 | tpy(π → π*) |
| 316 | 3.31 | tpy(π → π*) |
| 370 | 0.96 | Ru(dπ) → tpy(π*) CT |
| 516 | 0.99 | Ru(dπ) → tpy(π*) CT |
|  |  | Ru(dπ) → bpm(π*) CT |

[a]Absorption spectra taken in acetonitrile at room temperature.
[b]Lowest energy CT transitions taken from ref 32b.

The electronic absorption spectra for [{(tpy)RuCl(dpp)}$_2$RhCl$_2$]$^{3+}$ and [{(tpy)RuCl(bpm)}$_2$RhCl$_2$]$^{3+}$ in acetonitrile are characterized by high-energy tpy and BL (π to π*) transition, with tpy bands at 274 nm and 314 nm. A shoulder observed at ca. 340 or 360 nm is attributed to the BL (π to π*) transition for dpp and bpm, respectively.[31b] Significant spectral differences between these two trimetallics becomes apparent when the visible regions of the spectra are compared. The lowest energy transition at 540 nm for [{(tpy)RuCl(dpp)}$_2$RhCl$_2$]$^{3+}$, which contains the Ru(dπ) to dpp (π*) CT transition, is 116 nm higher in energy than the corresponding transition for the bpm analogue. This suggests that the impact of the rhodium coordination on the BL π* orbitals is more dramatic for bpm than dpp, consistent with the electrochemical behavior.[47]

A comparison of the electronic absorption spectra of the trimetallic, [{(tpy)RuCl(dpp)}$_2$RhCl$_2$]$^{3+}$, and its monometallic precursor, [(tpy)RuCl(dpp)]$^+$, reveals some interesting features. The UV regions of the spectra are virtually identical, consisting of dpp and tpy based π to π* transitions. As expected, these transitions are more intense for the trimetallic complex, in keeping with its molecular structure. Coordination of two monometallic precursors, [(tpy)RuCl(dpp)]$^+$, to the rhodium metal center red shifts the Ru(d π) to dpp(π*) CT transition from 516 nm for the monometallic to 540 nm. This results from rhodium coordination stabilizing the dpp-(π*) orbitals of the trimetallic, consistent with the electrochemical behavior of the title trimetallic. The Ru(dπ) to dpp(π*) CT band at 540 nm in [{(tpy)RuCl(dpp)}$_2$ RhCl$_2$]$^{3+}$ is red shifted relative to 514 nm in [{(bpy)$_2$Ru(dpp)}$_2$RhCl$_2$]$^{5+}$. This shift is due to higher energy Ru(dπ) orbitals in [{(tpy)RuCl(dpp)}$_2$RuCl$_2$]$^{3+}$ due to the coordinated chloride, also consistent with the electrochemical data.

The UV regions of the spectra for the bpm monometallic, [(tpy)RuCl(bpm)]$^+$, and the trimetallic, [{(tpy)RuCl(bpm)}$_2$RhCl$_2$]$^{3+}$, complexes are very similar, with intense intraligand π to π* transitions from bpm and tpy. Upon coordination of the monometallic to the rhodium metal center, the Ru(dπ) to bpm(π*) CT transition at 516 nm red shifts to 656 nm. This is the result of stabilization of the bpm(π*) orbitals from coordination of the electron-withdrawing rhodium center. This 656 nm Ru(dπ) to bpm(π*) CT transition of the title trimetallic is red shifted relative to the 594 nm peak in the bpy analogue [{(bpy)$_2$Ru(bpm)}$_2$RhCl$_2$]$^{5+}$, consistent with the electrochemical data.

Both title trimetallics [{(tpy)RuCl(BL)}$_2$RhCl$_2$]$^{3+}$ possess Ru(dπ) based HOMOs and Rh(dσ*) LUMOs. Spectroscopically, no optical transition is seen representing this metal-to-metal charge transfer (MMCT) excitation. This likely results from the high extinction coefficient for the lowest energy Ru(dπ) to BL(π*) CT transition and the low overlap of the Ru(dπ) and Rh(dσ*) orbitals leading to low intensity of the MMCT transition. Energetically, this MMCT state lies lower in energy than the optically populated MLCT state. This should lead to the intramolecular electron transfer to the Rh center in these complexes leading to quenching of the MLCT emission, discussed below.

This example demonstrates that these complexes are efficient light absorbers and that they undergo excitation into a metal to ligand charge transfer state with a high extinction coefficient. Additionally, this example demonstrates that the energy of this excitation can be tuned by simple component modification within this supramolecular architecture.

Example 4
Spectroelectrochemistry

Figure 6A:
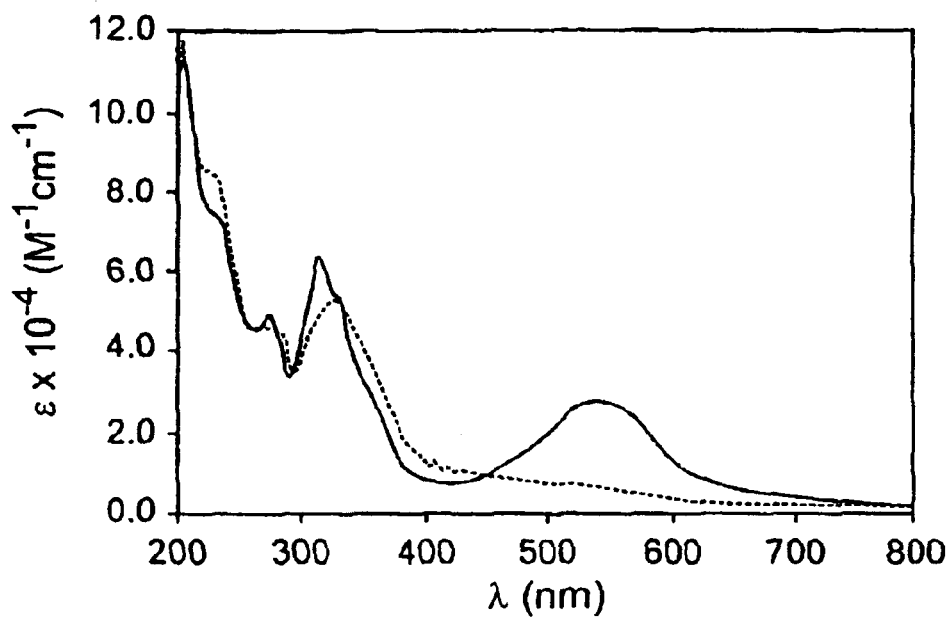
FIG. 6A and B. A, Spectroelectrochemistry for [{(tpy)RuCl(dpp)}$_2$RhCl$_2$](PF$_6$)$_3$ where tpy=2,2':6',2"-terpyridine and dpp=2,3-bis(2-pyridyl)pyrazine in 0.1 M Bu$_4$NPF$_6$ in CH$_3$CN at room temperature: (−) [{(tpy)RuCl(dpp)}$_2$RhCl$_2$]$^{3+}$, ( . . . ) [{(tpy)RuCl(dpp)}$_2$RhCl$_2$]$^{5+}$. B, Spectroelectrochemistry for [{(tpy)RuCl(bpm)}$_2$RhCl$_2$](PF$_6$)$_3$ where tpy=2,2':6',2"-terpyridine and bpm=2,2'-bipyrimidine in 0.1 M Bu$_4$NPF$_6$ in CH$_3$CN at room temperature: (−) [{(tpy)RuCl(bpm)}$_2$RhCl$_2$]$^{3+}$, ( . . . ) [{(tpy)RuCl(bpm)}$_2$RhCl$_2$]$^{5+}$.
Figure 6B:
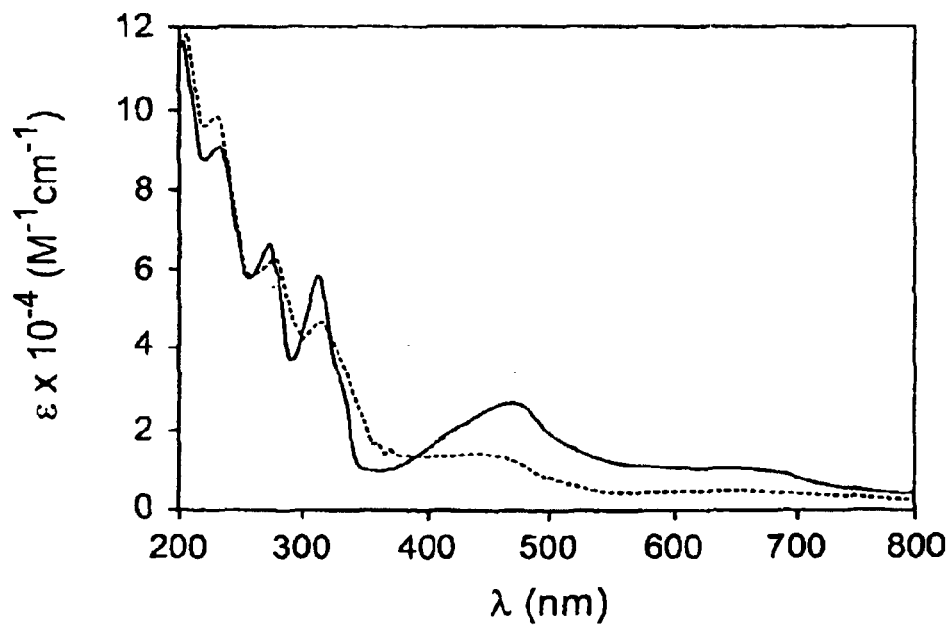

Spectroelectrochemistry was used to study the electronic absorption spectroscopy and cyclic voltammetry of the title trimetallics. The spectroelectrochemistry of [{(tpy)RuCl(dpp)}$_2$RhCl$_2$]$^{3+}$ and [{(tpy)RuCl(bpm)}$_2$RhCl$_2$]$^{3+}$ is shown in FIGS. 6A and 6B. The two-electron oxidation of [{(tpy)RuCl(dpp)}$_2$RhCl$_2$]$^{3+}$ is greater than 95% reversible. Electrolysis at 1.35 V, past the Ru$^{III/II}$ redox couple, shows a loss of the absorption band at 540 nm. This is consistent with its assignment as a Ru(dπ) to dpp(π*) CT transition. The absorption band at 314 nm and its lowest energy shoulder at 360 nm broaden and shift to lower energy upon oxidation of the ruthenium metal centers, consistent with a ligand-based (π to π*) transition.[31] A component (at ca. 330 nm) is lost upon oxidation of the ruthenium centers, consistent with a higher energy Ru(dπ) to tpy(π*) CT transition occurring in this region. Similar behavior has been reported for the oxidation of an array of Ru(tpy) moieties.[52,53] Reduction of the trimetallic complex was irreversible due to reaction of the reduced rhodium center, consistent with the Rh(dσ*) nature of the LUMO.

Very similar spectroelectrochemistry is observed for the bpm-bridged trimetallic, [{(tpy)RuCl(bpm)}$_2$RhCl$_2$]$^{3+}$, FIG. 6B. Oxidation of the ruthenium centers at 1.45 V is greater than 95% reversible. This electrolysis leads to the loss of the absorption bands at ca. 330, 464, and 656 nm, consistent with their assignment as higher energy Ru(d$\pi$) to tpy($\pi$*), Ru(d$\pi$) to tpy($\pi$*), and Ru(d$\pi$) to bpm($\pi$*) CT transitions, respectively. A broadening and red shift of the absorption band at 312 nm and shoulder at ca. 340 nm is consistent with overlapping intraligand $\pi$ to $\pi$* transitions. Reduction was irreversible, consistent with a Rh(d$\sigma$*) LUMO.

We were unable to detect any emission from the title trimetallics at room temperature or 77 K in acetonitrile solutions. This may result from the weak response of the photomultiplier tube in the region in which these complexes are expected to emit, a low quantum yield for emission, or a quenching of the MLCT excited state by the expected intramolecular electron transfer to the rhodium metal center. The [{(bpy)$_2$Ru(bpm)}$_2$RhCl2]$^{5+}$ system displays an emission at 800 nm,34 supporting the role of intramolecular electrontransfer quenching of the MLCT excited state in the title trimetallics in quenching their MLCT emission.

This example demonstrates that the nature of the lowest lying transition is metal to ligand charge transfer in character. Additionally, this example demonstrates the Rh-based nature of the LUMO allowing this Rh metal to function as an electron acceptor within this structural motif. This established the metal to metal nature of the lowest lying excited state of these complexes.

References for Examples 1 to 4

(1) Juris, A.; Balzani, V.; Barigelletti, F.; Campagna, S.; Belser, P.; von Zelewsky, A. *Coord. Chem. ReV.* 1988, 84, 85.
(2) Kalyanasundaram, K. *Coord. Chem. ReV.* 1982, 46, 159.
(3) (a) Strouse, G. F.; Schoonover, J. R.; Duesing, R.; Boyde, S.; Jones, W. E.; Meyer, T. J. *Inorg. Chem.* 1995, 34, 473.
(b) Durham, B.; Caspar, J. V.; Nagle, J. K.; Meyer, T. J. *J. Am. Chem. Soc.* 1982, 104, 4803.
(c) Anderson, P. A.; Strouse, G. F.; Treadway, J. A.; Keene, F. R.; Meyer, T. *J. Inorg. Chem.* 1996, 96, 759.
(4) Balzani, V.; Moggi, L.; Scandola, F. In *Supramolecular Photochemistry*; Balzani, V., Ed.; NATO ASI Series 214; Reidel: Dordrecht, 1987; p 1.
(5) Balzani, V.; Credi, A.; Raymo, F. M.; Stoddart, J. F. *Angew. Chem., Int. Ed.* 2000, 39, 3348.
(6) Balzani, V.; Juris, A. *Coord. Chem. ReV.* 2001, 211, 97.
(7) Balzani, V.; Ceroni, P.; Juris, A.; Venturi, M.; Campagna, S.; Puntoriero, F.; Serroni, S. *Coord. Chem. ReV.* 2001, 219–221, 545.
(8) (a) Balzani, V.; Juris, A.; Venturi, M.; Campagna, S.; Serroni, S. *Chem. ReV.* 1996, 96, 759.
(b) Balzani, V.; Campagna, S.; Dent, G.; Juris, A.; Seroni, S.; Venturi, M. *Acc. Chem. Res.* 1998, 31, 26.
(9) Sauvage, J.-P.; Collin, J.-P.; Chambron, J.-C.; Guillerez, S.; Coudret, C.; Balzani, V.; Barigelletti, F.; De Cola, L.; Flamigni, L. *Chem. ReV.* 1994, 94, 993.
(10) (a) Md. Meser, A.; MacDonnell, F. M. *J. Am. Chem. Soc.* 2000, 122, 11527.
(b) Flamigni, L.; Encinas, S.; Barigelletti, F.; MacDonnell, F. M.; Kim, K.-J.; Puntoriero, F.; Campagna, S. *Chem. Commun.* 2000, 13, 1185.
(c) Kim, M.-J., K.; MacDonnell, F. M.; Gimon-Kinsel, M. E.; DuBois, T.; Asgharian, N.; Griener, J. C. *Angew. Chem., Int. Ed.* 2000, 39, 615.
(d) MacDonnell, F. M.; Kim, M.-J.; Bodige, S. *Coord. Chem. Rev.* 1999, 185, 535.
(11) Petty, R. H.; Welch, B. R.; Wilson, L. J.; Bottomley, L. A.; Kadish, K. M. *J. Am. Chem. Soc.* 1980, 102, 611.
(12) Fuchs, Y.; Lofters, S.; Dieter, T.; Shi, W.; Morgan, S.; Strekas, T. C.; Gafney, H. D.; Baker, A. D. *J. Am. Chem. Soc.* 1987, 109, 2691.
(13) Hunziker, M.; Ludi, A. *J. Am. Chem. Soc.* 1977, 99, 7370.
(14) Brewer, K. J.; Murphy, W. R.; Spurlin, S. R.; Petersen, J. D. *Inorg. Chem.* 1986, 25, 882.
(15) Brauns, E.; Jones, S. W.; Clark, J. A.; Molnar, S. M.; Kawanishi, Y.; Brewer, K. J. *Inorg. Chem.* 1997, 36, 2861.
(16) Rillema, D. P.; Allen, G.; Meyer, T. J.; Conrad, D. *Inorg. Chem.* 1983, 22, 1617.
(17) Pavinato, R. A.; Walk, J. A.; McGuire, M. E. *Inorg. Chem.* 1993, 32, 1982.
(18) Young, R. C.; Nagle, J. K.; Meyer, T. J.; Whitten, D. G. *J. Am. Chem. Soc.* 1978, 100, 4773.
(19) Winkler, J. R.; Netzel, T. L.; Creutz, C.; Sutin, N. *J. Am. Chem. Soc.* 1987, 109, 2381.
(20) Berger, R. M.; McMillin, D. R. *Inorg. Chem.* 1988, 27, 4245.
(21) Arana, C. R.; Abruna, H. D. *Inorg. Chem.* 1993, 32, 194.
(22) Vogler, L. M.; Brewer, K. J. *Inorg. Chem.* 1996, 35, 818.
(23) Harriman, A.; Ziessel, R. *Coord. Chem. Commun.* 1998, 171, 331.
(24) Constable, E. C.; Housecroft, C. E.; Schofield, E. R.; Encinas, S.; Armaroli, N.; Barigelletti, F.; Flamigni, L.; Figgemeier, E.; Vos, J. G. *Chem. Commun.* 1999, 869.
(25) Indelli, M. T.; Bignozzi, C. A.; Scandola, F.; Collin, J. P. *Inorg. Chem.* 1998, 37, 6084.
(26) Duati, M.; Fanni, S.; Vos, J. G. *Inorg. Chem. Commun.* 2000, 3, 68.
(27) Hammarstrom, L.; Barigelletti, F.; Flamigni, L.; Indelli, M. T.; Armaroli, N.; Calogero, G.; Guardigli, M.; Sour, A.; Collin, J. P.; Savauge, J. P. *J. Phys. Chem.* 1997, 101, 9061.
(28) Maestri, M.; Armaroli, N.; Balzani, V.; Constable, E. C.; Thompson, A. M. *Inorg. Chem.* 1995, 34, 2759.
(29) Jones, S. W.; Jordan, M. R.; Brewer, K. J. In *Molecular and Supramolecular Photochemistry*; Schanze, K. S., Ed.; Marcel Dekker: New York, 1999; Vol. 4, p 151.
(30) Brewer, K. J. *Comments Inorg. Chem.* 1999, 21, 201.
(31) (a) Molnar, S. M.; Nallas, G. N.; Bridgewater, J. S.; Brewer, K. J. *J. Am. Chem. Soc.* 1994, 116, 5206.
(b) Bridgewater, J. S.; Vogler, L. M.; Molnar, S. M.; Brewer, K. J. *Inorg. Chim. Acta* 1993, 208, 179.
(32) (a) Rasmussen, S. C.; Richter, M. M.; Yi, E.; Pace, H.; Brewer, K. J. *Inorg. Chem.* 1990, 29, 3926.
(b) Molnar, S. M.; Jensen, G. E.; Vogler, L. M.; Jones, S. W.; Laverman, L.; Bridgewater, J. S.; Richter, M. M.; Brewer, K. J. *J. Photochem. Photobiol., A: Chem.* 1994, 80, 315.
(33) Nallas, G. N. A.; Brewer, K. J. *Inorg. Chim. Acta* 1996, 253, 7.
(34) Nallas, G. N.; Jones, S. W.; Brewer, K. J. *Inorg. Chem.* 1996, 35, 6974.
(35) Kalyanasundaram, K.; Gratzel, M.; Nazeeruddin, Md. K. *J. Phys. Chem.* 1992, 96, 5865.
(36) (a) Indelli, M. T.; Scandola, F.; Collin, J.-P.; Sauvage, J.-P.; Sour, A. *Inorg. Chem.* 1996, 35, 303.
(b) Indelli, M. T.; Scandola, F.; Flamingni, L.; Collin, J.-P. Sauvage, J.-P. Sour, A. *Inorg. Chem.* 1997, 36, 4247.
(37) Scandola, F.; Argazzi, R.; Bignozzi, A.; Indelli, M. T. *J. Photochem. Photobiol., A: Chem.* 1994, 82, 191.
(38) Nozaki, K.; Ohno, T.; Haga, M. *J. Phys. Chem.* 1992, 96, 10880.

(39) Watzky, M. A.; Endicott, J. F.; Song, X.; Lei, Y.; Macatangay, A. *Inorg. Chem.* 1996, 35, 3463.

(40) Lee, J. D.; Vrana, L. M.; Bullock, E. R.; Brewer, K. *J. Inorg. Chem.* 1998, 37, 3575.

(41) (a) Lei, Y.; Buranda, T.; Endicott, J. F. *J. Am. Chem. Soc.* 1990, 112, 8820.
(b) Macatangay, A. V.; Mazzetto, S. E.; Endicott, J. F. *Inorg. Chem.* 1999, 38, 5091.

(42) Nawar, N. *J. Organomet. Chem.* 1999, 590, 217.

(43) da Silva, A. C.; Piotrowski, H.; Mayer, P.; Polbom, K.; Severin, K. *Eur. J. Inorg. Chem.* 2001, 3, 685.

(44) Ranco, S. E.; Thompson, D. W.; Gahan, S. L.; Petersen, J. D. *Inorg. Chem.* 1998, 27, 2020.

(45) Sullivan, B. P.; Calvert, J. M.; Meyer, T. *J. Inorg. Chem.* 1980, 19, 1404.

(46) Vogler, L. M.; Franco, C.; Jones, S. W.; Brewer, K. *J. Inorg. Chim. Acta* 1994, 221, 55.

(47) Swavey, S.; Fang, Z.; Brewer, K. *J. Inorg. Chem.*, in press.

(48) Gennett, T.; Milner, D. F.; Weaver, M. J. *J. Phys. Chem.* 1985, 89, 2787.

(49) Brewer, K. J.; Calvin, M.; Lumpkin, R. S.; Otvos, J. W.; Spreer, L. O. *Inorg. Chem.* 1989, 28, 4446.

(50) (a) Kew, G.; DeArmond, K.; Hanck, K. *J. Phys. Chem.* 1974, 78, 727. (b) Kew, G.; Hanck, K.; DeArmond, K. *J. Phys. Chem.* 1975, 79, 1828.

(51) Krause, E.; Ferguson, J. *Prog. Inorg. Chem.* 1989, 37, 293.

(52) Vrana, L. M.; Brewer, K. J. *J. Photochem. Photobiol., A* 1997, 109, 2013.

(53) *J. Organomet. Chem.* 1998, 554, 29.

Background for Example 5

Recent emphasis has been placed on developing reagents capable of cleaving DNA, applicable as structural probes and therapeutic agents, with many transition metal complexes being reported.[1-18] Photochemical approaches are of particular interest as they offer reaction control and can be highly targeted.[10-15,19] One popular approach involves the sensitization of molecular oxygen.[5,7,8,20]

The development of photosensitizers that absorb low energy light, are tunable, and function in the absence of molecular oxygen is of interest. Oxygen independent systems function under conditions of low oxygen content and often have a different mechanism of photocleavage.[16] A photosensitizer which can be excited with low energy light can avoid the base damage induced by UV light.[21,22]

Rhodium and ruthenium complexes photocleave DNA. Photolysis at 310 nm of rhodium(III) complexes of phi (9,10-phenanthrenequinone diimine) leads to hydrogen abstraction from the 3'-carbon of deoxyribose, leading to DNA cleavage.[23] Cleavage selectivity can be modulated by ancillary[4] and active[25] ligand variation or by tethering to DNA.[26-29] [Rh(phi)$_2$(phen)]$^{3+}$ has recently been shown to stabilize duplex DNA inhibiting transcription.30 Rh$_2$(O$_2$CCH$_3$)$_4$L$_2$ (L=H$_2$O$_{14}$ or PPh$_3$ [31]) has exhibited the ability to photocleave DNA when irradiated in the presence of electron acceptors. Studies have shown site specific oxidative cleavage of DNA using [Ru$^{IV}$(tpy)(bpy)O]$^{2+}$ and [Ru$^{III}$(tpy)(bpy)OH]$^{2+}$(tpy=2,2':6',2"-terpyridine.[32,33] Photoexcitation of ruthenium(II) (polypyridyl systems has resulted in oxidative damage to DNA in the presence of an electron acceptor[34-36] and cleavage by oxygen sensitization.[5,7,8] Rh(III) complexes intercalated into DNA serve as electron acceptors for excited Ru chromophores via long-range electron transfer.[37,38]

Figure 7A:
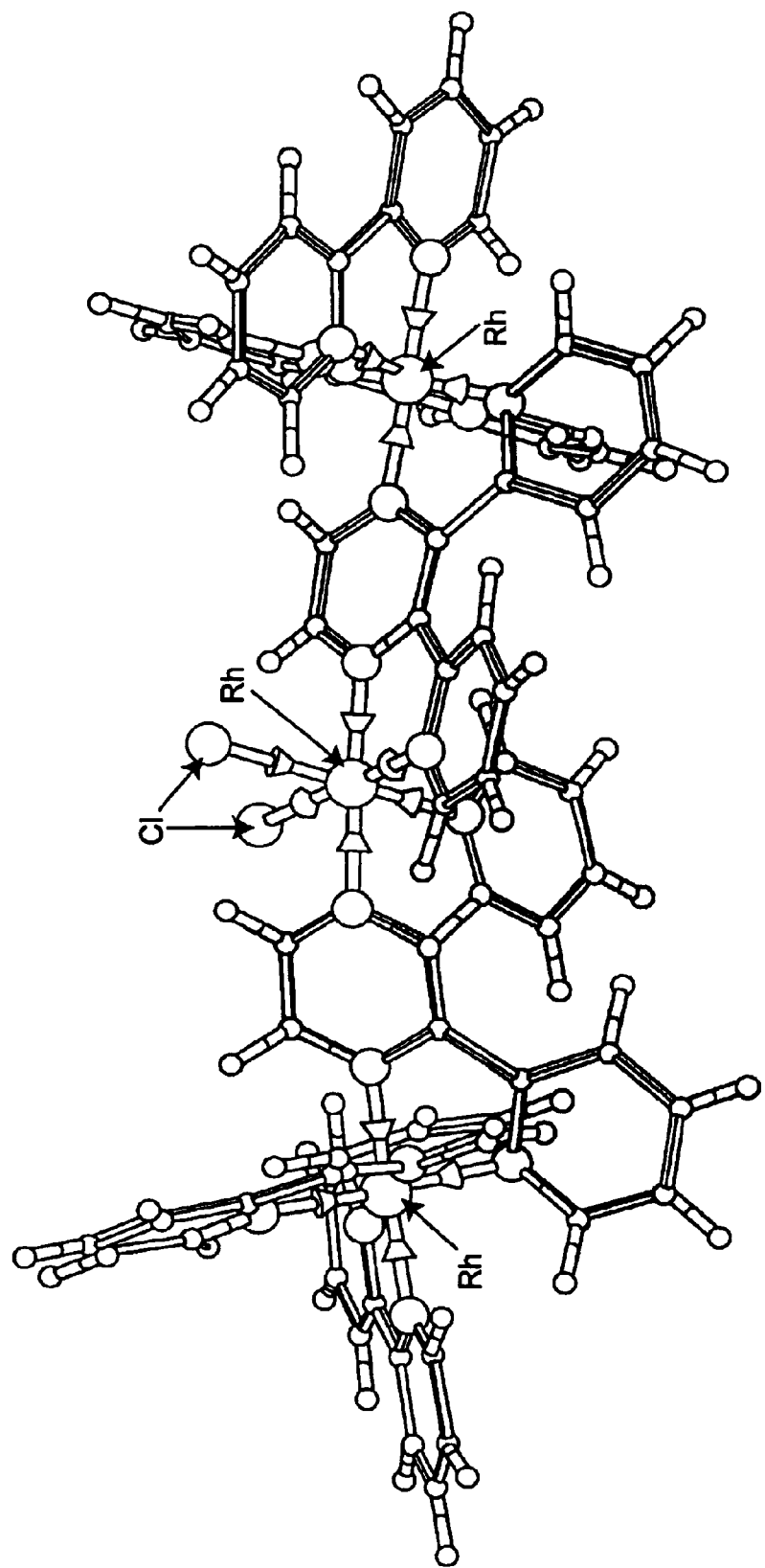
FIG. 7A and B. Representations of the mixed-metal trimetallic complex [{(bpy)$_2$Ru(dpp)}$_2$RhCl$_2$]$^{5+}$.
Figure 7B:
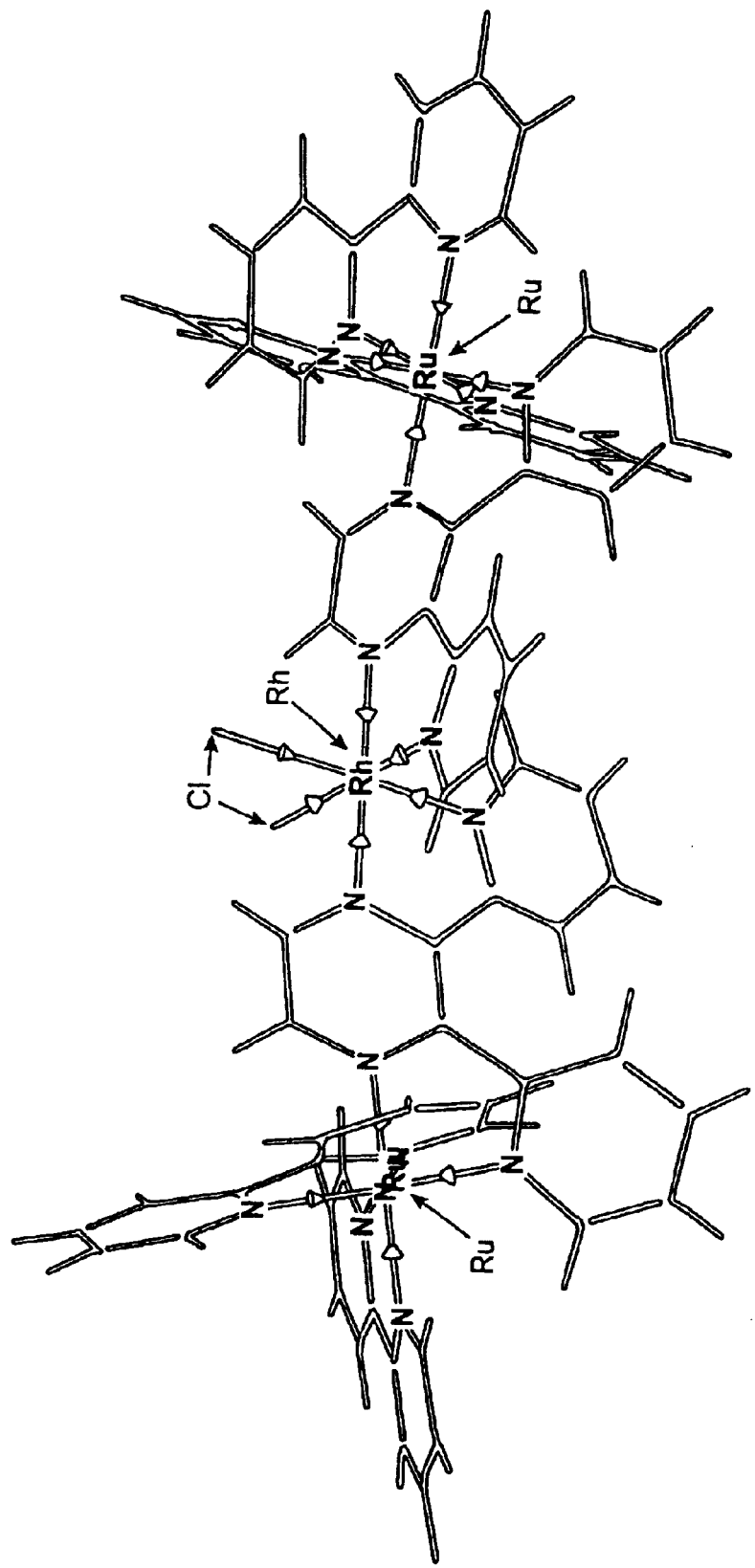

Trimetallic complexes coupling light absorbing ruthenium centers to reactive metal centers have been of interest. [{(bpy)$_2$Ru(BL)}$_2$MCl$_2$]$^{5+}$(M=Rh or Ir and BL=2,3-bis(2-pyridyl)pyrazine (dpp)[39] or 2,2'-bipyrimidine (bpm)[40]) complexes, shown in FIG. 7 display quite varied electrochemical properties and differing lowest lying excited states. They are good chromophores with the high energy region of the electronic absorption spectra dominated by ligand based ($\pi$ to $\pi^*$) transitions. The visible region contains metal to ligand charge transfer (MLCT) transitions to both acceptor ligands with the BL transition being the lowest energy.

Figure 8:
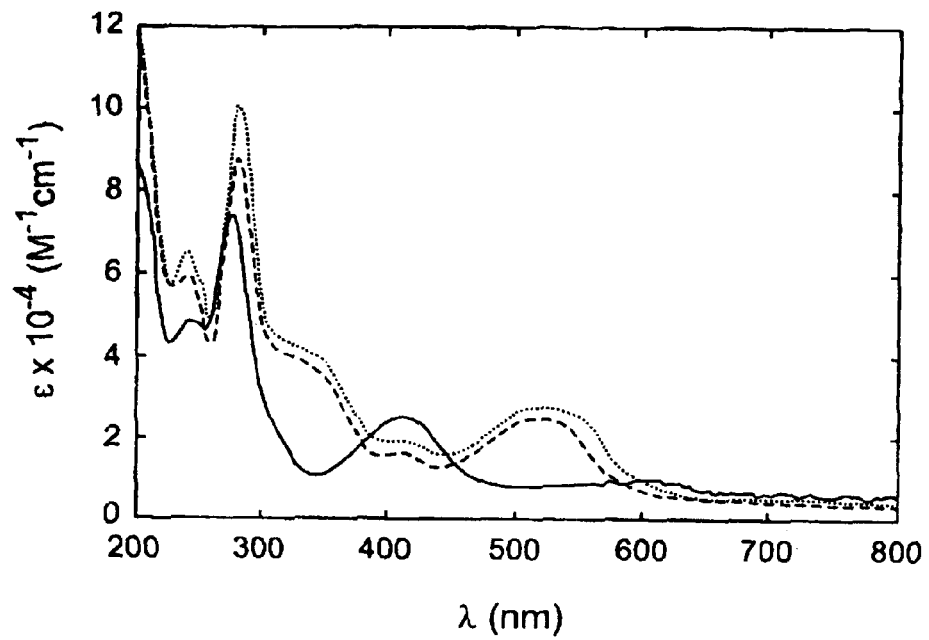
FIG. 8. Electronic absorption spectra for [{(bpy)$_2$Ru(bpm)}$_2$RhCl$_2$]$^{5+}$ (s), [{(bpy)$_2$Ru(dpp)}$_2$RhCl$_2$]$^{5+}$( - - - ), and [{(bpy)$_2$Ru(dpp)}$_2$IrCl$_2$]$^{5+}$( . . . ) in doubly distilled water, ddH$_2$O.
Figure 9:
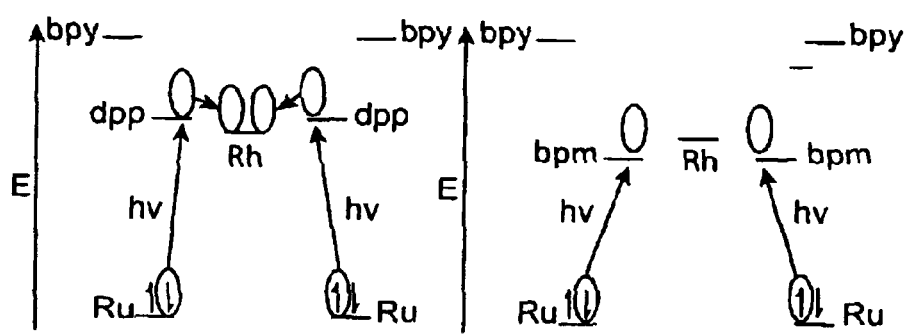
FIG. 9. Orbital Energy Diagram for [{(bpy)$_2$Ru(dpp)}$_2$RhCl$_2$]$^{5+}$ and [{(bpy)$_2$Ru(bpm)}$_2$RhCl$_2$]$^{5+}$ FIGS. 10A–C. (a) Schematic representations of imaged agarose gel showing the photocleavage of pUC18 plasmid by [{(bpy)$_2$Ru(dpp)}$_2$RhCl$_2$]$^{5+}$ in the absence of molecular oxygen. Lane 1 λ molecular weight standard, lanes 2 and 3 plasmid controls, lanes 4 and 6 plasmid incubated at 37° C. (2 h) in the presence of [(bpy)$_2$Ru(dpp)]$^{2+}$ and [{(bpy)$_2$Ru(dpp)}$_2$RhCl$_2$]$^{5+}$, respectively (1:5 metal complex/base pair), lanes 5 and 7 plasmid irradiated at λ≧475 nm for 10 min in the presence of [(bpy)$_2$Ru(dpp)]$^{2+}$ and [{(bpy)$_2$Ru(dpp)}$_2$RhCl$_2$]$^{5+}$, respectively. (b) Lanes 1 and 2 plasmid controls, lanes 3 and 5 plasmid incubated at 37° C. (3 h) in the presence of [{(bpy)$_2$Ru(bpm)}$_2$RhCl$_2$]$^{5+}$ and [{(bpy)$_2$Ru(dpp)}$_2$IrCl$_2$]$^{5+}$, respectively, lanes 4 and 6 plasmid irradiated at λ≧475 nm for 10 min in the presence of [{(bpy)$_2$Ru(bpm)}$_2$RhCl$_2$]$^{5+}$ and [{(bpy)$_2$Ru(dpp)}$_2$IrCl$_2$]$^{5+}$, respectively. (c) Imaged agarose gel showing photocleavage of pBluescript plasmid in the absence of molecular oxygen by [(bpy)$_2$Ru(dpp)RhCl$_2$(dpp)Ru(bpy)$_2$](PF$_6$)$_5$. Lane 1 is the λ molecular weight standard, lane 2 is the control linearized DNA (cut with HindIII) with no metal present, lane 3 is the control circular DNA with no metal present, lane 4 is a 1:5 metal complex/base pair mixture of the plasmid with the metal complex incubated at 37° C. (4 h), and lane 5 is a 1:5 metal complex/base pair mixture of the plasmid with the metal complex photolyzed at 520±5 nm for 4 h. All gels used 0.8% agarose, 90 mM Tris, and 90 mM boric acid buffer (pH=8.2, ionic strength=0.0043 M calculated using the Henderson-Hasselbalch equation).

The electronic absorption spectra of these supramolecular complexes are shown in FIG. 8. All three complexes possess lowest lying Ru(dic) to BL CT bands that occur in the low energy visible region. For [{(bpy)$_2$Ru(dpp)}$_2$RhCl$_2$]$^{5+}$ and [{(bpy)$_2$Ru(dpp)}$_2$IrCl$_2$]$^{5+}$, the Ru(d$\pi$) to dpp($\pi^*$) CT transition occurs at 525 nm. The Ru(d$\pi$) to bpm($\pi$ to $\pi^*$) CT transition for [{(bpy)$_2$Ru(bpm)}$_2$RhCl$_2$]$^{5+}$ occurs at 594 nm. The Ir and Rh analogues, [{(bpy)$_2$Ru(dpp)}$_2$MCl$_2$]$^{5+}$, have spectroscopy that is virtually identical owing to their similar supramolecular structure and the dominance of the Ru light absorbers on the spectroscopic properties of these systems. The electrochemical properties vary with BL and M for [{(bpy)$_2$Ru(BL)}$_2$MCl$_2$]$^{5+}$, summarized in Table 3. The complexes exhibit a single reversible oxidation wave in the anodic region (1.56 and 1.70 V vs Ag/AgCl) attributed to the overlapping Ru$^{III/II}$ redox couple for the two equivalent Ru centers. [{(bpy)$_2$Ru(bpm)}$_2$RhCl$_2$]$^{5+}$ exhibits reversible bridging ligand reductions prior to reduction of the central Rh metal.[40] [{(bpy)$_2$Ru(dpp)}$_2$RhCl$_2$]$^{5+}$ undergoes an irreversible two electron reduction of the Rh($\pi^*$) metal center prior to reduction of the dpp BL. This orbital inversion, FIG. 9, of the dpp($\pi^*$) and Rh(d$\sigma^*$) orbitals, allows the Rh to function as an electron acceptor giving a lowest lying, Ru to Rh metal to metal charge transfer (MMCT) excited state in this complex. It is this state we exploit for DNA photocleavage.

TABLE 3

Electrochemical Properties for a Series of Ru(II) and Ru(II)/Rh(III)/Ru(II) Trimetallic Complexes where bpy = 2,2'-Bipyridine, dpp = 2,3-Bis(2-pyridyl)pyrazine, and bpm = 2,2'-Bipyrimidine complex

| Complex | $E_{1/2}$, V[a] | assignment |
|---|---|---|
| [{(bpy)$_2$Ru(dpp)}$_2$RhCl$_2$](PF$_6$)$_5$ | 1.6 | 2Ru$^{III/II}$ |
| | −0.39[b] | Rh$^{III/I}$ |
| | −0.79 | dpp,dpp/dpp,dpp$^-$ |
| | −1.02 | dpp,dpp$^-$/dpp$^-$dpp$^-$ |
| [{(bpy)$_2$Ru(bpm)}$_2$RhCl$_2$](PF$_6$)$_5$ | 1.7 | 2Ru$^{III/II}$ |
| | −0.13 | bpm,bpm/bpm,bpm |
| | −0.26 | bpm,bpm$^-$/bpm$^-$,bpm$^-$ |
| | −0.78 | Rh$^{III/I}$ |
| [{(bpy)$_2$Ru(dpp)}$_2$IrCl$_2$](PF$_6$)$_5$ | 1.56 | Rh$^{III/I}$ |
| | −0.39 | dpp,dpp/dpp,dpp$^-$ |
| | −0.54 | dpp,dpp$^-$/dpp dpp |

[a]Potentials reported versus the Ag/AgCl (0.29 V vs NHE) reference electrode in 0.1 M Bu$_4$NPF$_6$,CH$_3$CN.
[b]$E_p^c$ value.

Example 5

Photocleavage of DNA with Trimetallic Supramolecular Complexes

The lack of a Rh(d$\sigma^*$) LUMO in the [{(bpy)$_2$Ru(bpm)}$_2$RhCl$_2$]$^{5+}$ system allowed us to use this as a very similar supramolecular architecture control system with a lowest lying MLCT state. The Ir analogue, [{(bpy)$_2$Ru(dpp)}$_2$IrCl$_2$]$^{5+}$, served as a spectroscopically matched system with a lowest lying MLCT state.

pUC18 and pBluescript were used to probe photocleavage of DNA by gel electrophoresis.[14,26,41,42] pUC18 plasmid is 2686 bp (Bayou Biolabs). Irradiation used a 1000 W xenon arc lamp, a water IR filter, and a 475 nm cut off filter. Solutions were 3.5 $\mu$M in metal complex and 6.9 mM in phosphate buffer (pH=7) and allowed for ionic association of the cationic metal complexes with DNA. Dexoygenation was accomplished by bubbling with Ar for 30 min prior to the photolysis of the samples in an airtight cell blanketed with Ar.

Figure 10A:
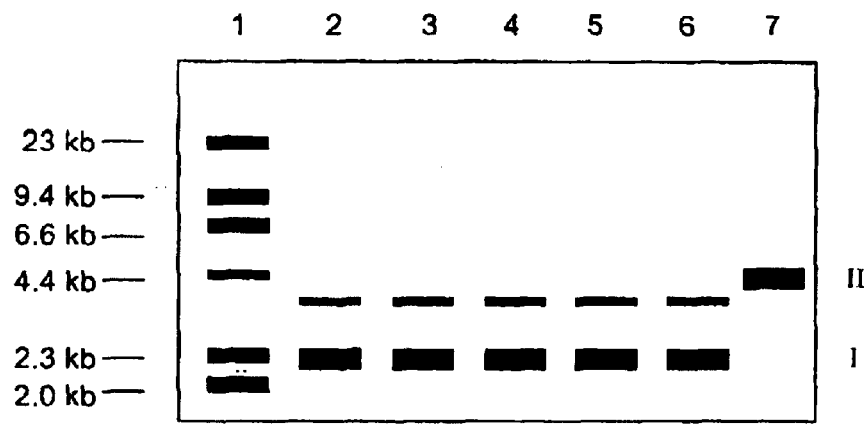
Figure 10B:
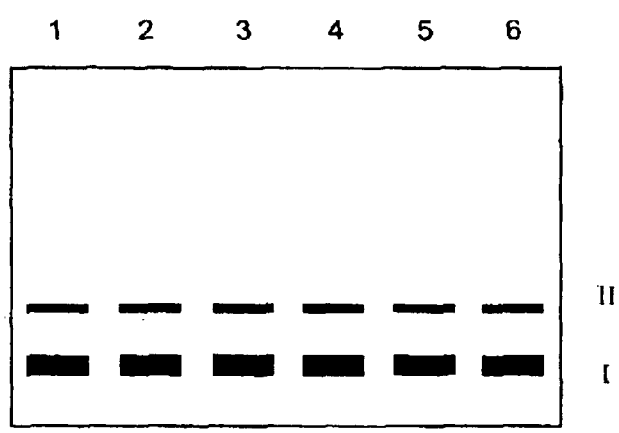
Figure 10C:
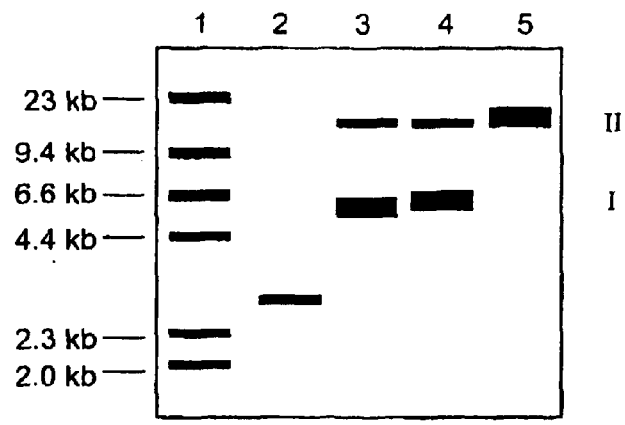

FIG. 10 shows imaged ethidium bromide stained agarose gels that reveal that the excited state of $[\{(bpy)_2Ru(dpp)\}_2RhCl_2]^{5+}$ photocleaves DNA. Lane 1 (FIG. 10a) shows the $\lambda$ molecular weight standard. Lane 2 (FIG. 10a) indicates that pUC18 plasmid is found mostly as the supercoiled state (form I) with a small amount of nicked, circular DNA (form II). When irradiated ($\lambda_{irr} \geq 475$ nm) for 10 min, the plasmid alone (lane 3) does not cleave.[42] When incubated at 37° C. for 2 h in the presence of the monometallic precursor, $[(bpy)_2Ru(dpp)]^{2+}$ (lane 4), or in the presence of the trimetallic complex, $[\{(bpy)_2Ru(dpp)\}_2RhCl_2]^{5+}$(lane 6), the plasmid DNA is not cleaved. When irradiated for 10 min in the presence of the monometallic precursor (lane 5), no evidence for DNA cleavage is observed. In the absence of molecular oxygen when the plasmid is irradiated for 10 min ($\lambda_{irr} \geq 475$ nm) in the presence of $[\{(bpy)_2Ru(dpp)\}_2RhCl_2]^{5+}$ at a 1:5 metal complex to base pair ratio (lane 7), conversion of the supercoiled DNA to the nicked form is observed. FIG. 10c, lane 5, shows a similar cleavage of pBluescript plasmid using a narrow band excitation. These cleavage reactions are also observed in the presence of molecular oxygen. The photocleavage of DNA by $[\{(bpy)_2Ru(dpp)\}_2RhCl_2]^{5+}$ but not the monometallic ruthenium synthon illustrates the role of the supramolecular architecture, including Rh, on the desired photoreactivity. The cleavage product migrates slightly slower through the gel than native nicked plasmid, and similar results have been observed by Turro.[14]

To explore the role of the Rh LUMO, resulting in an MMCT excited state, on the DNA photocleavage, the bpm analogue $[\{(bpy)_2Ru(bpm)\}_2RhCl_2]^{5+}$ and the Ir analogue $[\{(bpy)_2Ru(dpp)\}_2IrCl_2]^{5+}$, which contain inaccessible Rh(d$\sigma$*) and Ir(d$\sigma$*) orbitals,[39,40] were studied for their ability to photocleave DNA. The Ir analogue has nearly identical electronic absorption spectroscopy to that of the Rh complex. This allows it to function well as a control system possessing a lowest lying MLCT state. The results of this study are shown in FIG. 10b. Lanes 1 and 2 (FIG. 10b) are the plasmid controls. Lanes 3 and 5 reveal that when the plasmid is incubated at 37° C. in the presence of $[\{(bpy)_2Ru(bpm)\}_2RhCl_2]^{5+}$ or $[\{(bpy)_2Ru(dpp)\}_2IrCl_2]^{5+}$, respectively, at a 1:5 metal complex to base pair ratio, no DNA cleavage occurs. Similar solutions irradiated ($\lambda_{irr} \geq 475$ nm) for 10 min (lanes 4 and 6), in the absence of molecular oxygen, also do not result in DNA cleavage. Similar studies in the presence of oxygen also do not result in DNA cleavage.

These results indicate that our mixed-metal supramolecular complex, $[\{(bpy)_2Ru(dpp)\}_2RhCl_2]^{5+}$, is capable of DNA photocleavage and similar systems without a Rh(d$\sigma$*) based LUMO do not display this behavior. This illustrates that our modifications of the coordination environment, yielding the desired orbital ordering, $[\{(bpy)_2Ru(dpp)\}_2RhCl_2]^{5+}$, creates a system that photocleaves DNA via an MMCT excited state. Additionally, photocleavage can occur in the absence of molecular oxygen.

This study presents a new structural motif for DNA photocleavage agents, functioning from a previously unstudied excited state for this application. A frank cleavage is observed consistent with reactivity arising from the photogenerated Rh(II) site. This supramolecular architecture allows for substitution of components to tune properties of these systems, allowing for the development of many new complexes that should display similar reactivity.

References for Example 5

(1) Absalon, M. J.; Wu, w.; Stubbe, J. *Biochemistry* 1995, 34, 2076.
(2) Tullius, T. D. *Nature* 1988, 332, 663.
(3) Sardesai, N. Y.; Zimmermann, K.; Barton, J. K. *J. Am. Chem. Soc.* 1994, 116, 7502.
(4) Mrksich, M.; Dervan, P. B. *J. Am. Chem. Soc.* 1995, 117, 3325.
(5) Hergueta-Bravo, A.; Jimenez-Hemandez, M. E.; Montero, F.; Oliveros, E.; Orellana, G. *J. Phys. Chem. B.* 2002, 106, 4010.
(6) Juskowiak, B.; Dominiak, A.; Takenaka, S.; Takagi, M. *Photochem. Photobiol.* 2001, 74, 391.
(7) Moucheron, C.; Kirsch-DeMesmaeker, A.; Kelly, J. M. *J. Photochem. Photobiol., B* 1997, 40, 91.
(8) Tossi, A. B.; Kelly, J. M. *Photochem. Photobiol.* 1989, 49, 545.
(9) Barton, J. K.; Raphael, A. L. *Proc. Natl. Acad. Sci. U.S.A.* 1985, 82, 6460.
(10) Barton, J. K.; Holmlin, R. E. *Inorg. Chem.* 1995, 34, 7.
(11) Fleisher, M. B.; Waterman, K. C.; Turro, N. J.; Barton, J. K. *Inorg. Chem.* 1986, 25, 3549.
(12) Bhattacharya, S.; Mandal, S. S. *Chem. Commun.* 1996, 1515.
(13) Farinas, E.; Tan, J. D.; Baidya, N.; Mascharak, P. K. *J. Am. Chem. Soc.* 1993, 115, 2996.
(14) Fu, P. K.-L.; Bradley, P. M.; Turro, C. *Inorg. Chem.* 2001, 40, 2476.
(15) Nunez, M. E.; Rajski, S. R.; Barton, J. K. *Methods Enzymol.* 2000, 319, 165.
(16) Armitage, B. *Chem. ReV.* 1998, 98, 1171.
(17) Dunn, D. A.; Lin, V. H.; Kochevar, I. E. *Biochemistry* 1992, 31, 11620.
(18) Paillous, N.; Vincendo, P. *J. Photochem. Photobiol., B* 1993, 20, 203.
(19) Kim, J.; Sistarc, M. F.; Carter, P. J.; Thorp, H. H. *Coord. Chem. ReV.* 1998, 171, 341.
(20) Bonnett, R. *Chemical Aspects of Photodynamic Therapy*; Taylor and Francis, Inc.: Philadelphia, 2000; Vol. 1, Chapter 4, pp 57–70.
(21) Boutorine, A. S.; Brault, D.; Takasugi, M.; Delgado, O.; Helene, C. *J. Am. Chem. Soc.* 1996, 118, 9469.
(22) Murray, V.; Martin, R. *Nucleic Acids Res.* 1994, 22, 506.
(23) Sitlani, A.; Long, E. C.; Pyle, A. M.; Barton, J. K. *J. Am. Chem. Soc.* 1992, 114, 2303.
(24) Turro, C.; Hall, D. B.; Chen, W.; Zuilhof, H.; Barton, J. K.; Turro, N. J. *J. Phys. Chem. A* 1998, 102, 5708.
(25) (a) Jackson, B. A.; Henling, L. M.; Barton, J. K. *Inorg. Chem.* 1999, 38, 6218. (b) Jackson, B. A.; Barton, J. K. *Biochemistry* 2000, 39, 6176.
(26) Copeland, K. D.; Fitzsimons, M. P.; Houser, R. P.; Barton, J. K. *Biochemistry* 2002, 41, 343.
(27) Williams, T. T.; Barton, J. K. *J. Am. Chem. Soc.* 2002, 124, 1840.
(28) Hall, D. B.; Holmlin, R. E.; Barton, J. K. *Nature* 1996, 382, 731.
(29) Nunez, M. E.; Barton, J. K. *Curr. Opin. Chem. Biol.* 2000, 4, 199.
(30) Fu, P. K.-L.; Turro, C. *Chem. Commun.* 2001, 279.
(31) Bradley, P. M.; Fu, P. K.-.L.; Turro, C. *Comments Inorg. Chem.* 2001, 22, 393.

(32) Cheng, C. C.; Goll, J. G.; Neyhart, G. A.; Walch, T. W.; Singh, P.; Thorp, H. H. *J. Am. Chem. Soc.* 1995, 117, 2970.
(33) Farrer, B. T.; Thorp, H. H. *Inorg. Chem.* 2000, 39, 44.
(34) Stemp, E. D. A.; Arkin, M. R.; Barton, J. K. *J. Am. Chem. Soc.* 1997, 119, 2921.
(35) Delaney, S.; Pascaly, M.; Bhattacharya, P. K.; Han, K.; Barton, J. K. *Inorg. Chem.* 2002.
(36) Ambroise, A.; Maiya, B. G. *Inorg. Chem.* 2000, 39, 4264.
(37) Purugganan, M. D.; Kumar, C. V.; Turro, N. J. *Science* 1988, 241, 1645.
(38) Arkin, M. R.; Stemp, E. D. A.; Holmlin, R. E.; Barton, J. K.; Hormann, A.; Olsen, E. J. C.; Barbara, P. F. *Science* 1996, 273, 475.
(39) Molnar, S. M.; Jensen, G. E.; Vogler, L. M.; Jones, S. W.; Laverman, L.; Bridgewater, J. S.; Richter, M. M.; Brewer, K. J. *J. Photochem. Photobiol., A* 1994, 80, 315.
(40) Nallas, G. N.; Jones, S. W.; Brewer, K. *J. Inorg. Chem.* 1996, 35, 6974.
(41) Kumar, C. V.; Tan, W. B.; Betts, P. W. *J. Inorg. Biochem.* 1997, 68, 177.

Figure 11A:
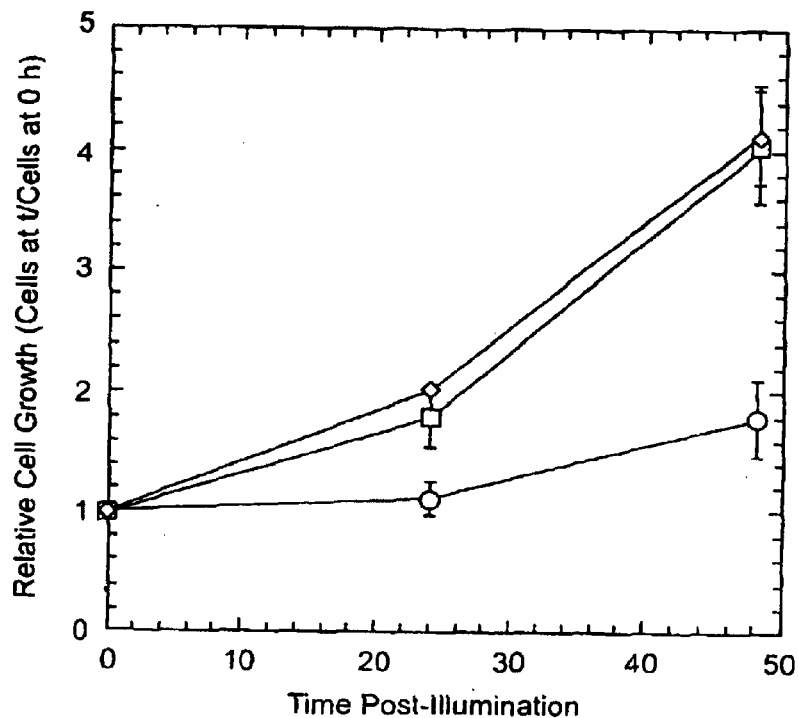
FIGS. 11A and B. A, Photochemically induced inhibition of cell replication: time course. x axis=time post illumination in minutes; y axis=relative cell growth. B, Photochemically induced inhibition of cell replication: effect of varying concentrations of complex. x axis=concentration of [{(bpy)$_2$Ru(dpp)}$_2$RhCl$_2$]Cl$_5$; y axis=relative cell growth.

Example 6
Photoinduced Inhibition of Cell Replication with $[\{(bpy)_2Ru(dpp)\}_2RhCl_2](PF_6)_5$ Photoinduced inhibition of Vero cell replication by the supramolecular complex $[\{(bpy)_2Ru(dpp)\}_2RhCl_2](PF_6)_5$ was investigated. All experiments were carried out with 0.5 mg/mL of $[\{(bpy)_2Ru(dpp)\}_2RhCl_2](PF_6)_5$ in MEM media, and the results are shown in FIG. 11A. This cell line normally replicates once each 24 hours. The line with diamond symbols (◇) shows the growth of the Vero cells after irradiation for 10 minutes at $\lambda > 475$ nm. As can be seen, exposure to light alone did not impact this replication. The line with square symbols (□) shows the results obtained when Vero cells are incubated in the dark with various concentrations of $[\{(bpy)_2Ru(dpp)\}_2RhCl_2](PF_6)_5$. As can be seen, exposure to $[\{(bpy)_2Ru(dpp)\}_2RhCl_2](PF_6)_5$ alone (i.e. without illumination) did not impact replication.

In marked contrast, photolysis at $\lambda > 475$ nm after incubation with $[\{(bpy)_2Ru(dpp)\}_2RhCl_2](PF_6)_5$ greatly inhibits cell replication, as evidenced by the line with circle symbols (○).

This example demonstrates that the complex $[\{(bpy)_2Ru(dpp)\}_2RhCl_2](PF_6)_5$ is not toxic to cells in the dark. It further demonstrates that the complex $[\{(bpy)_2Ru(dpp)\}_2RhCl_2](PF_6)_5$ is able to greatly inhibit the replication of cells after exposure of cells with this complex to low energy visible light. Thus, the complexes of the present invention display photodynamic action leading to inhibition of cell replication.

Figure 11B:
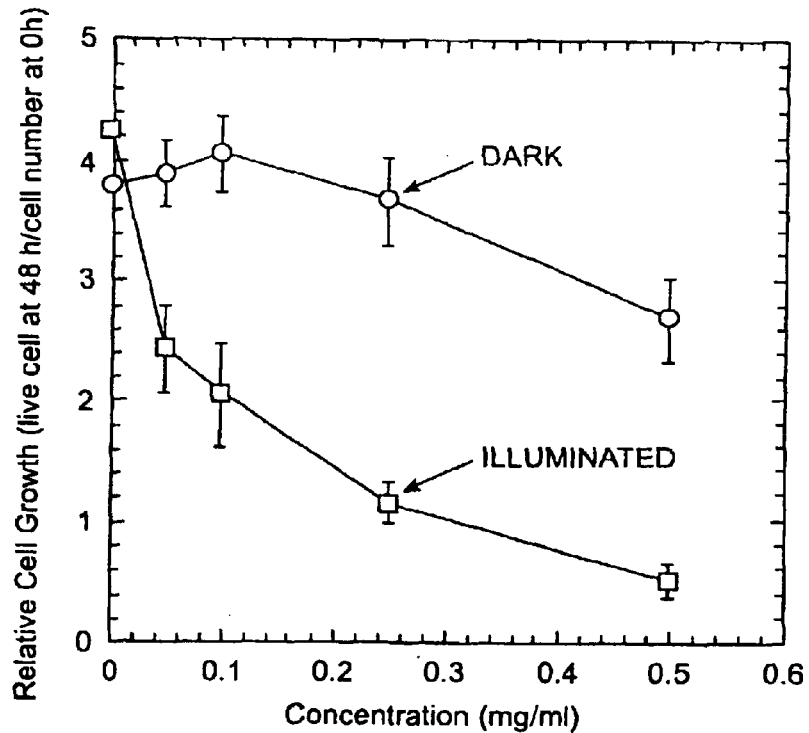

Example 7
Concentration Dependance of Photoinduced Inhibition of Cell Replication with $[\{(bpy)_2Ru(dpp)\}_2RhCl_2]Cl_5$ The concentration dependence of photoinduced inhibition of cell replication by the supramolecular complex $[\{(bpy)_2Ru(dpp)\}_2RhCl_2]Cl_5$ is shown in FIG. 11B. The line with circular symbols shows the impact on Vero cell growth of the incubation of the cells in the dark with the indicated concentrations of $[\{(bpy)_2Ru(dpp)\}_2RhCl_2]Cl_5$. The line with square symbols shows the growth of Vero cells incubated with the same concentrations of $[\{(bpy)_2Ru(dpp)\}_2RhCl_2]Cl_5$, and subsequent irradiation for 10 minutes at $\lambda > 475$ nm. As can be seen, irradiation at $\lambda > 475$ nm greatly inhibits the ability of Vero cells to replicate. This is likely due to photoinduced death of the irradiated cells.

This example demonstrates that the complex $[\{(bpy)_2Ru(dpp)\}_2RhCl_2]Cl_5$ is not toxic to cells in the dark at a wide range of concentrations. It further demonstrates that the complex $[\{(bpy)_2Ru(dpp)\}_2RhCl_2]Cl_5$ is able to greatly inhibit the replication of cells after exposure of cells with this complex to low energy visible light and demonstrates the concentration needed for such action. Thus, the complexes of the present invention display photodynamic action leading to inhibition of cell replication.

Example 8
Photocleavage of DNA with Various Supramolecular Metallic Complexes

Figure 12A:
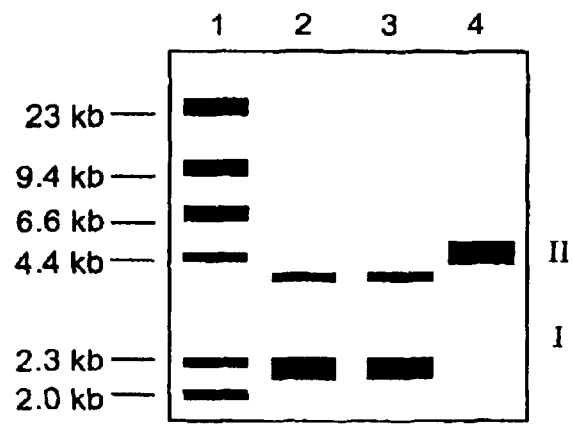
FIGS. 12A–C. DNA Photocleavage by Various Supramolecular Metallic Complexes. Schematic representation of analysis of cleavage patterns by gel electrophoresis.
Figure 12B:
Figure 12C:
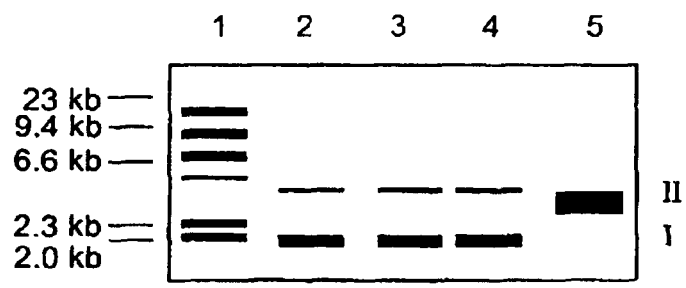

The ability of several supramolecular complexes to photocleave DNA was assayed and the results are shown in FIGS. 12A–C. Details of the experiments are given in the figure legends. The complexes utilized were A, $[\{(bpy)_2Os(dpp)\}_2RhCl_2](PF_6)_5$; B, $[\{(tpy)RuCl(dpp)\}_2RhCl_2](PF_6)_3$; and C, $[\{(tpy)RuCl(bpm)\}_2RhCl_2](PF_6)_3$. As can be seen, each complex displayed the ability to efficiently cleave DNA upon activation by low energy, visible light.

This example demonstrates that many components as described herein can be successfully incorporated into the generic supramolecular metallic complex of the present invention and result in the production of a complex that successfully cleaves DNA.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for decreasing the replication of hyperproliferating cells, comprising the steps of
delivering to said cells a supramolecular complex comprising
at least one metal to ligand charge transfer (MLCT) light absorbing metal;
at least one bridging π-acceptor ligand; and
an electron acceptor metal;
and
applying light or radiant energy to said hyperproliferating cells, wherein said step of applying light to said hyperproliferating cells induces the production of a metal-to-metal charge transfer state within said supramolecular complex, and wherein said metal-to-metal charge transfer state mediates the cleavage of DNA of said hyperproliferating cells, thereby causing a decrease in the replication of said hyperproliferating cells.

2. The method of claim 1 wherein said at least one metal to ligand charge transfer (MLCT) light absorbing metal is selected from the group consisting of ruthenium(II), osmium (III), rhenium(I), iron(II) and platinum(II).

3. The method of claim 1, wherein said at least one bridging π-acceptor ligand is selected from the group consisting of 2,3-bis(2-pyridyl)pyrazine; 2,2'-bipyridimidine; 2,3-bis(2-pyridyl)quinoxaline; and 2,3,5,6,-tetrakis(2-pyridyl)pyrazine.

4. The method of claim 1, wherein said electron acceptor metal is selected from the group consisting of rhodium(III), platinum(IV), cobalt(III), and iridium(III).

5. The method of claim 1, wherein said supramolecular complex further comprises at least one terminal π-acceptor ligand.

6. The method of claim 5, wherein said at least one terminal π-acceptor ligand is selected from the group consisting of 2,2'-bipyridine; 2,2':6',2"-terpyridine; triphenylphosphine; and 2,2'-phenylpyridine and diethylphenylphosphine.

7. The method of claim 1 wherein said light is visible light.

8. The method of claim 1 wherein said supramolecular complex is selected from the group consisting of

[(2,2'-bipyridine)$_2$ Ru(2-pyridyl)pyrazine)RhCl$_2$(2-pyridyl)pyrazine)Ru(2,2'-bipyridine)$_2$](PF$_6$)$_5$;

[(2,2'-bipyridine)$_2$Os(2,3-bis(2-pyridyl)pyrazine)RhCl$_2$ (2,3-bis(2-pyridyl)pyrazine)Os(2,2'-bipyridine)$_2$] (PF$_6$)$_5$;

[(2,2':6',2"-terpyridine)RuCl(2,3-bis(2-pyridyl)pyrazine) RhCl$_2$(2,3-bis(2-pyridyl)pyrazine)RuCl(2,2':6',2"-terpyridine)](PF$_6$)$_3$; and

[(2,2':6',2"-terpyridine)RuCl(2,2'-bipyridimidine)RhCl$_2$ (2,2'-bipyridimidine)RuCl(2,2':6',2"-terpyridine)] (PF$_6$)$_3$.

9. The method of claim 1 wherein said hyperproliferating cells are cancer cells selected from the group consisting of leukemia cells, ovarian cancer cells, Burkitt's lymphoma cancer cells, breast cancer cells, gastric cancer cells, and testicular cancer cells.

10. A method for decreasing the replication of hyperproliferating cells, comprising the steps of delivering to said hyperproliferating cells a supramolecular complex comprising
at least one metal to ligand charge transfer (MLCT) light absorbing metal;
at least one bridging π-acceptor ligand; and
an electron acceptor metal;

and inducing the production of a metal-to-metal charge transfer state within said supramolecular complex by the application of light, thereby causing a decrease in replication of said hyperproliferating cells.

* * * * *